United States Patent
Zhang et al.

(10) Patent No.: US 11,612,751 B2
(45) Date of Patent: Mar. 28, 2023

(54) STIMULATION CONFIGURATION VARIATION TO CONTROL EVOKED TEMPORAL PATTERNS

(71) Applicant: Boston Scientific Neuromodulation Corporation, Valencia, CA (US)

(72) Inventors: Tianhe Zhang, Studio City, CA (US); Rosana Esteller, Santa Clarita, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 244 days.

(21) Appl. No.: 16/741,228

(22) Filed: Jan. 13, 2020

(65) Prior Publication Data

US 2020/0147393 A1    May 14, 2020

Related U.S. Application Data

(63) Continuation-in-part of application No. 16/460,655, filed on Jul. 2, 2019, now Pat. No. 11,338,127, and a
(Continued)

(51) Int. Cl.
*A61N 1/36*        (2006.01)
*A61N 1/02*        (2006.01)
(Continued)

(52) U.S. Cl.
CPC ......... *A61N 1/36175* (2013.01); *A61N 1/025* (2013.01); *A61N 1/0551* (2013.01);
(Continued)

(58) Field of Classification Search
CPC ............ A61N 1/36175; A61N 1/36062; A61N 1/36071; A61N 1/36132; A61N 1/36135;
(Continued)

(56) References Cited

U.S. PATENT DOCUMENTS 5,697,958 A    12/1997  Paul et al.
5,702,429 A    12/1997  King
(Continued)

FOREIGN PATENT DOCUMENTS

CN    202933390    5/2013
EP    2923727      9/2015
(Continued)

OTHER PUBLICATIONS

U.S. Appl. No. 62/825,982, Wagenbach et al., filed Mar. 29, 2019.
(Continued)

*Primary Examiner* — Mark W. Bockelman
(74) *Attorney, Agent, or Firm* — Lewis & Reese, PLLC

(57) ABSTRACT

Methods and systems for programming stimulation parameters for an implantable medical device for neuromodulation, such as spinal cord stimulation (SCS) are disclosed. The stimulation parameters define user-configured waveforms having at least a first phase having a first polarity and a second phase having a second polarity, wherein the first and second phases are separated by an interphase interval (IPI). By delivering user-configured waveforms with different IPIs, stimulation geometry, and other waveform settings, therapeutic asynchronous activation of dorsal column fibers can be obtained.

17 Claims, 19 Drawing Sheets

Related U.S. Application Data continuation-in-part of application No. 16/100,904, filed on Aug. 10, 2018, now Pat. No. 10,576,282.

(60) Provisional application No. 62/803,003, filed on Feb. 8, 2019, provisional application No. 62/544,656, filed on Aug. 11, 2017.

(51) Int. Cl.
*A61N 1/05* (2006.01)
*A61B 5/24* (2021.01)

(52) U.S. Cl.
CPC ..... *A61N 1/36062* (2017.08); *A61N 1/36071* (2013.01); *A61N 1/36132* (2013.01); *A61N 1/36135* (2013.01); *A61N 1/36182* (2013.01); *A61B 5/24* (2021.01)

(58) Field of Classification Search
CPC .. A61N 1/025; A61N 1/36182; A61N 1/0551; A61N 1/36164; A61N 1/36139; A61N 1/36178; A61B 5/24; A61B 5/686; A61B 5/407; A61B 5/6877
See application file for complete search history.

(56) References Cited

U.S. PATENT DOCUMENTS

| | | | |
|---|---|---|---|
| 5,902,236 | A | 5/1999 | Iversen |
| 5,902,249 | A | 5/1999 | Lyster |
| 5,913,882 | A | 6/1999 | King |
| 6,181,969 | B1 | 1/2001 | Gord et al. |
| 6,516,227 | B1 | 2/2003 | Meadows et al. |
| 7,024,247 | B2 | 4/2006 | Gliner et al. |
| 7,424,322 | B2 | 9/2008 | Lombardi et al. |
| 7,450,992 | B1 | 11/2008 | Cameron |
| 7,603,177 | B2 | 10/2009 | Sieracki et al. |
| 8,180,451 | B2 | 5/2012 | Hickman et al. |
| 8,255,057 | B2 | 8/2012 | Fang et al. |
| 8,335,664 | B2 | 12/2012 | Eberle |
| 8,352,030 | B2 | 1/2013 | Denison |
| 8,359,102 | B2 | 1/2013 | Alataris et al. |
| 8,515,546 | B2 | 8/2013 | Goddard et al. |
| 8,606,362 | B2 | 12/2013 | He et al. |
| 8,620,436 | B2 | 12/2013 | Parramon et al. |
| 8,712,533 | B2 | 4/2014 | Alataris et al. |
| 8,792,988 | B2 | 7/2014 | Alataris et al. |
| 9,044,155 | B2 | 6/2015 | Strahl |
| 9,155,892 | B2 | 10/2015 | Parker et al. |
| 9,248,274 | B2 | 2/2016 | Troosters et al. |
| 9,248,279 | B2 | 2/2016 | Chen et al. |
| 9,259,574 | B2 | 2/2016 | Aghassian et al. |
| 9,265,431 | B2 | 2/2016 | Hincapie Ordonez et al. |
| 9,302,112 | B2 | 4/2016 | Bornzin et al. |
| 9,327,125 | B2 | 5/2016 | Alataris et al. |
| 9,333,357 | B2 | 5/2016 | Alataris et al. |
| 9,381,356 | B2 | 7/2016 | Parker et al. |
| 9,386,934 | B2 | 7/2016 | Parker et al. |
| 9,403,013 | B2 | 8/2016 | Walker et al. |
| 9,409,020 | B2 | 8/2016 | Parker |
| 9,446,243 | B2 | 9/2016 | Marnfeldt et al. |
| 9,480,842 | B2 | 11/2016 | Alataris et al. |
| 9,526,897 | B2 | 12/2016 | Chen et al. |
| 9,533,148 | B2 | 1/2017 | Carcieri et al. |
| 9,731,116 | B2 | 8/2017 | Chen |
| 9,789,252 | B2 | 10/2017 | Gerber et al. |
| 9,872,990 | B2 | 1/2018 | Parker et al. |
| 9,937,344 | B2 * | 4/2018 | Starkebaum ....... A61N 1/36007 |
| 9,974,455 | B2 | 5/2018 | Parker et al. |
| 10,076,667 | B2 | 9/2018 | Kaula et al. |
| 10,786,677 | B2 * | 9/2020 | Parramon .......... A61N 1/36146 |
| 2002/0156513 | A1 | 10/2002 | Borkan |
| 2005/0246004 | A1 | 11/2005 | Cameron et al. |
| 2008/0146894 | A1 | 6/2008 | Bulkes et al. |
| 2010/0023090 | A1 | 1/2010 | Jaax et al. |
| 2010/0274312 | A1 | 10/2010 | Alataris et al. |
| 2012/0092031 | A1 | 4/2012 | Shi et al. |
| 2012/0095519 | A1 | 4/2012 | Parramon et al. |
| 2012/0095529 | A1 | 4/2012 | Parramon et al. |
| 2013/0053923 | A1 | 2/2013 | Jaax et al. |
| 2013/0268026 | A1 | 10/2013 | Rao et al. |
| 2013/0289665 | A1 | 10/2013 | Marnfeldt et al. |
| 2013/0345773 | A1 | 12/2013 | Grill et al. |
| 2014/0194772 | A1 | 7/2014 | Single et al. |
| 2014/0236042 | A1 | 8/2014 | Parker et al. |
| 2014/0277251 | A1 | 9/2014 | Gerber et al. |
| 2014/0296737 | A1 | 10/2014 | Parker et al. |
| 2014/0364919 | A1 | 12/2014 | Doan |
| 2015/0080982 | A1 | 3/2015 | Funderburk |
| 2015/0157861 | A1 | 6/2015 | Aghassian et al. |
| 2015/0231402 | A1 | 8/2015 | Aghassian |
| 2015/0282725 | A1 | 10/2015 | Single et al. |
| 2015/0313487 | A1 | 11/2015 | Single et al. |
| 2015/0335893 | A1 | 11/2015 | Parker |
| 2015/0360038 | A1 | 12/2015 | Zottola et al. |
| 2016/0082265 | A1 | 3/2016 | Moffitt et al. |
| 2016/0114166 | A1 | 4/2016 | Kaula et al. |
| 2016/0144183 | A1 | 5/2016 | Marnfeldt |
| 2016/0158551 | A1 | 6/2016 | Kent et al. |
| 2016/0166164 | A1 | 6/2016 | Obradovic et al. |
| 2016/0228705 | A1 | 8/2016 | Crowder et al. |
| 2016/0287126 | A1 | 10/2016 | Parker et al. |
| 2016/0287182 | A1 | 10/2016 | Single et al. |
| 2016/0317815 | A1 | 11/2016 | Doan et al. |
| 2016/0361543 | A1 | 12/2016 | Kaula et al. |
| 2016/0367822 | A1 | 12/2016 | Parramon |
| 2017/0049345 | A1 | 2/2017 | Single et al. |
| 2017/0056642 | A1 | 3/2017 | Moffitt et al. |
| 2017/0071490 | A1 | 3/2017 | Parker et al. |
| 2017/0106197 | A1 | 4/2017 | Wechter et al. |
| 2017/0135624 | A1 | 5/2017 | Parker et al. |
| 2017/0165490 | A1 | 6/2017 | Wechter |
| 2017/0173335 | A1 | 6/2017 | Min et al. |
| 2017/0189685 | A1 | 7/2017 | Steinke et al. |
| 2017/0216587 | A1 | 8/2017 | Parker et al. |
| 2017/0296823 | A1 | 10/2017 | Hershey et al. |
| 2017/0361101 | A1 | 12/2017 | Single et al. |
| 2018/0043172 | A1 | 2/2018 | Serrano Carmona |
| 2018/0064943 | A1 | 3/2018 | Grill et al. |
| 2018/0071513 | A1 | 3/2018 | Weiss et al. |
| 2018/0071520 | A1 | 3/2018 | Weerakoon et al. |
| 2018/0071527 | A1 | 3/2018 | Feldman et al. |
| 2018/0104493 | A1 | 4/2018 | Doan et al. |
| 2018/0110987 | A1 | 4/2018 | Parker et al. |
| 2018/0117335 | A1 | 5/2018 | Parker et al. |
| 2018/0132747 | A1 | 5/2018 | Parker et al. |
| 2018/0132760 | A1 | 5/2018 | Parker et al. |
| 2018/0133459 | A1 | 5/2018 | Parker et al. |
| 2018/0140831 | A1 | 5/2018 | Feldman et al. |
| 2018/0214699 | A1 | 8/2018 | Kothandaraman et al. |
| 2018/0228391 | A1 | 8/2018 | Parker et al. |
| 2018/0228547 | A1 | 8/2018 | Parker et al. |
| 2018/0256052 | A1 | 9/2018 | Parker et al. |
| 2018/0280691 | A1 | 10/2018 | Ackermann et al. |
| 2019/0046800 | A1 | 2/2019 | Doan et al. |
| 2019/0083796 | A1 | 3/2019 | Weerakoon et al. |
| 2019/0099602 | A1 | 4/2019 | Esteller et al. |
| 2019/0175915 | A1 | 6/2019 | Brill et al. |
| 2019/0209844 | A1 | 7/2019 | Esteller et al. |
| 2019/0275331 | A1 | 9/2019 | Zhu |
| 2019/0290900 | A1 | 9/2019 | Esteller et al. |
| 2019/0299006 | A1 | 10/2019 | Marnfeldt |
| 2019/0344083 | A1 | 11/2019 | Marnfeldt et al. |
| 2019/0366094 | A1 | 12/2019 | Esteller et al. |
| 2019/0366104 | A1 | 12/2019 | Doan et al. |
| 2020/0009367 | A1 | 1/2020 | Huertas Fernandez et al. |
| 2020/0009394 | A1 | 1/2020 | Huertas Fernandez et al. |

FOREIGN PATENT DOCUMENTS

| | | |
|---|---|---|
| EP | 3381507 A1 | 10/2018 |
| WO | 2009/048580 A1 | 4/2009 |
| WO | 2015/077362 | 5/2015 |
| WO | 2016/172239 A1 | 10/2016 |

(56) References Cited

FOREIGN PATENT DOCUMENTS

| WO | 2017/100866 | 6/2017 |
| WO | 2017/106539 | 6/2017 |
| WO | 2017/173493 | 10/2017 |
| WO | 2017/210352 | 12/2017 |
| WO | 2017/219096 | 12/2017 |

OTHER PUBLICATIONS

U.S. Appl. No. 62/849,642, Zhang et al., filed May 17, 2019.
U.S. Appl. No. 62/860,627, Esteller et al., filed Jun. 12, 2019.
U.S. Appl. No. 16/657,560, Moffitt et al., filed Oct. 18, 2019.
U.S. Appl. No. 16/661,549, Esteller et al., filed Oct. 23, 2019.
H. Mino & J. Rubenstein, "Effects of Neural Refractoriness on Spatio-Temporal Variability in Spike Initiations with Eletrical Stimulation," IEEE Trans. On Neural Sys. & Rehabilitation Eng., vol. 14, No. 3, pp. 273-280 (2006).
M. Moffit et al., A Novel 3-Dimensional Algorithm for Model-Based Programming in Spinal Cord Stimuation (SCS): Illumina-3D™, presentation (2013).
M. Hughes, "Fundamentals of Clinical ECAP Measures in Cochlear Implants: Part 1: Use of the ECAP in Speech Processor Programming (2nd Ed.)," Audiology Online (Nov. 8, 2010) (http://www.audiologyonline.com/articles/fundamentalsclinicalecapmeasuresin846).
I. Akhoun et al., "Electrically evoked compound action potential artifact rejection by independent component analysis: Technique validation," Hearing Research 302, pp. 60-73 (2013).
J. Rubinstein et al., "Pseudospontaneous activity: stochastic independence of auditory nerve fibers with electrical stimulation," Hear Res., 127(1-2), pp. 108-118 (1999) (abstract only).
J. Paz, "Physiological Midline Mapping Based on Spinal Cord Stimulation (SCS) Response Using the 32-Contact Paddle Lead," 19th NANS Annual Meeting (Dec. 13-15, 2015).
E.L. Air et al., "Electrophysiologic Monitoring for Placement of Laminectomy Leads for Spinal Cord Stimulation Under General Anesthesia," Neuromodulation: Technology at the Neural Interface, vol. 15(6), pp. 573-580 (2012).
J.L. Shils et al., "Intraoperative Neurophysiologic Methods for Spinal Cord Stimulator Placement Under General Anesthesia," Neuromodulation: Technology at the Neural Interface, vol. 15(6), pp. 560-572 (2012).
A. Taghva et al., "Intraoperative Electromyography as an Adjunct to Sacral Neuromodulation for Chronic Pelvic Pain," Neuromodulation: Technology at the Neural Interface, vol. 18(1), pp. 62-66 (2015).
L. Kapural et al., "Novel 10-kHz High-frequency Therapy (HF10 Therapy) Is Superior to Traditional Low-frequency Spinal Cord Stimulation for the Treatment of Chronic Back and Leg Pain," Anesthesiology 2015; 123:851-60 (Oct. 2015).
S. Thomson et al., "The PROCO Randomised Controlled Trial: Effects of Pulse Rate On Clinical Outcomes in Kilohertz Frequency Spinal Cord Stimulation—A Multicentre, Double-blind, Crossover Study," presented at the International Neuromodulation Society (INS) Meeting on May 31, 2017.
E.C. Celik et al., "The effect of low-frequency TENS in the treatment of neuropathic pain in patients with spinal cord injury," Spinal Cord 51:34-337 (2013).
Y. Maeda et al., "Low frequencies, but not high frequencies of bi-polar spinal cord stimulation reduce cutaneous and muscle hyperalgesia induced by nerve injury," Pain 138:143-152 (2008).
S. Thomson et al., "Neural Dosing and Energy Requirements in Kilohertz Frequency Spinal Cord Stimulation (SCS)," poster presented at the International Neuromodulation Society (INS) Meeting on May 31, 2017.
S. Paz et al., "Improved Efficacy of SCS Implants Using Multiple Waveforms and Field Shape Options," poster presented at the International Neuromodulation Society (INS) Meeting on May 31, 2017.
S. Paz et al., "Evaluation of Customized Field Shape for Subperception SCS in a Case Series of Chronic Pain Patients," poster presented at the North American Neuromodulation Society (NANS) Meeting on Jan. 11-14, 2018.
S.J. Thomson et al., "Effects of Rate on Analgesia in Kilohertz Frequency Spinal Cord Stimulation: Results of the PROCO Randomized Controlled Trial," Neuromodulation: Technology at the Neural Interface, vol. 21(1), pp. 67-76 (2018) (published on-line Dec. 8, 2017).
J.M. North et al., "Clinical Outcomes of 1 kHz Subperception Spinal Cord Stimulation in Implanted Patients With Failed Paresthesia-Based Stimulation: Results of a Prospective Randomized Controlled Trial," Neuromodulation: Technology at the Neural Interface, vol. 19(7), pp. 731-737 (2016).
Yearwood, Thomas, et al., Handout titled "A Prospective Comparison of Spinal Cord Stimulation (SCS) Using Dorsal Column Stimulation (DCS), Intraspinal Nerve Root Stimulation (INRS), and Varying Pulse Width in the Treatment of Chronic Low Back Pain," Congress of Neurological Surgeons 56th Annual Meeting, Oct. 7-12, 2006, 2 pages.
Yearwood, Thomas, et al., Poster titled "A Prospective Comparison of Spinal Cord Stimulation (SCS) Using Dorsal Column Stimulation (DCS), Intraspinal Nerve Root Stimulation (INRS), and Varying Pulse Width in the Treatment of Chronic Low Back Pain," Congress of Neurological Surgeons 56th Annual Meeting, Oct. 7-12, 2006, 7 pages.
Yearwood, Thomas, "Neuropathic Extremity Paid and Spinal Cord Stimulation," Pain Medicine, vol. 7, No. SI, 2006, 6 pages.
International Search Report and Written Opinion regarding corresponding PCT Application No. PCT/US2020/013341, dated Apr. 6, 2020.

\* cited by examiner

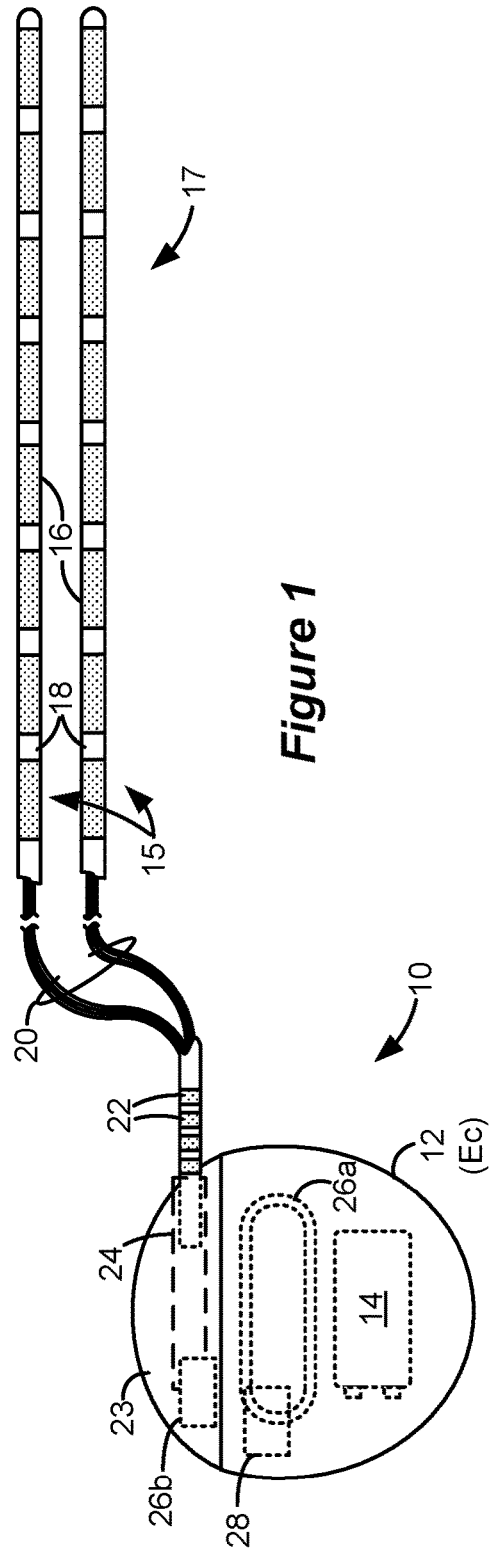
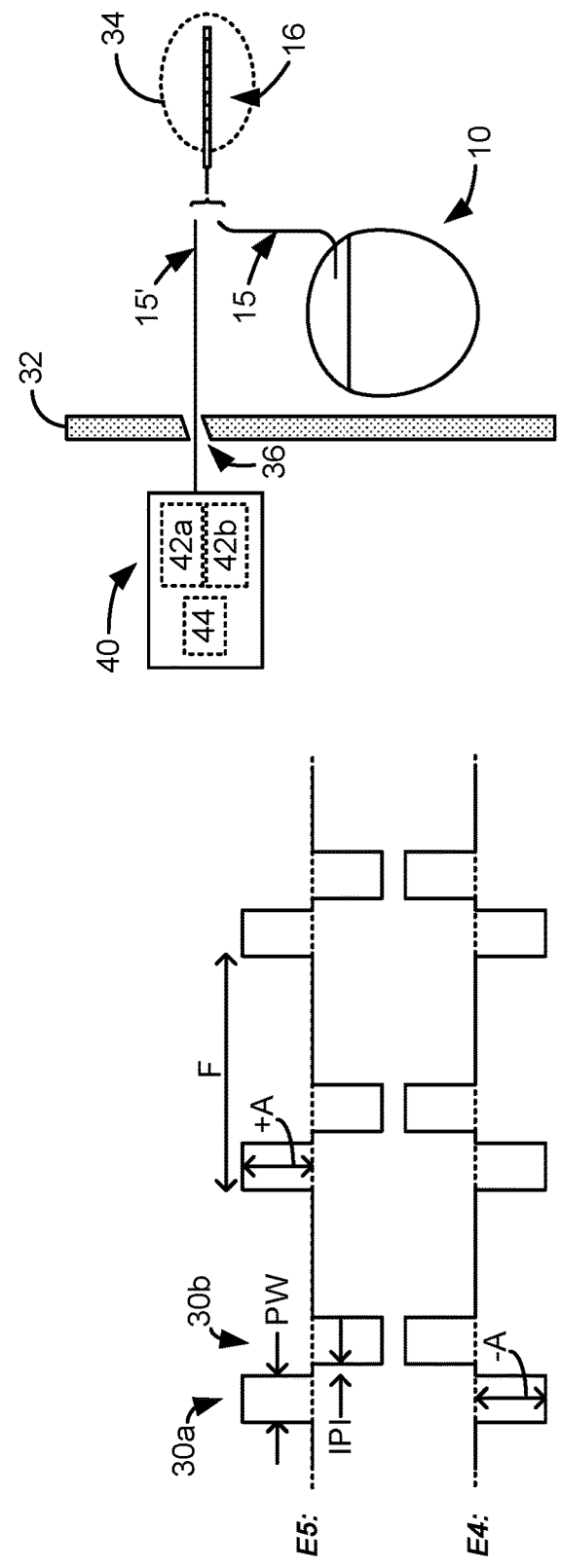
Figure 1
Figure 2
Figure 3

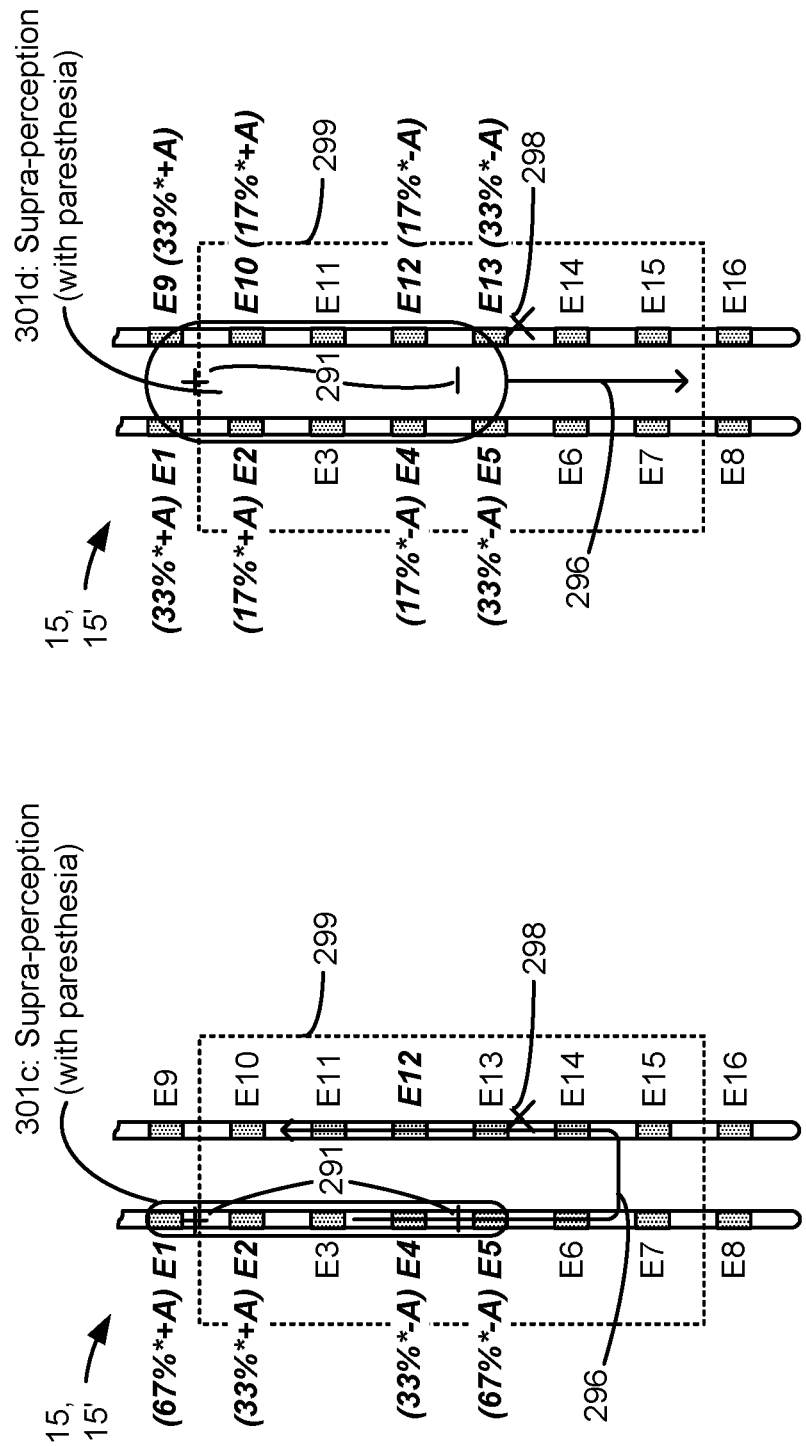

STIMULATION CONFIGURATION VARIATION TO CONTROL EVOKED TEMPORAL PATTERNS

CROSS REFERENCE TO RELATED APPLICATIONS

This application is a non-provisional application of U.S. Provisional Patent Application Ser. No. 62/803,003, filed Feb. 8, 2019.

This application is also a continuation-in-part of U.S. patent application Ser. No. 16/100,904, filed Aug. 10, 2018, which is a non-provisional application of U.S. Provisional Patent Application Ser. No. 62/544,656, filed Aug. 11, 2017.

This application is also a continuation-in-part of U.S. patent application Ser. No. 16/460,655, filed Jul. 2, 2019.

Priority is claimed to these above-referenced applications, and all are incorporated by reference in their entireties.

FIELD OF THE INVENTION

This application relates to Implantable Medical Devices (IMDs), generally, Spinal Cord Stimulators, more specifically, and to methods of controlling such devices to deliver user-configured stimulation.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable neurostimulator device system.

SUMMARY

Methods and systems for programming an implantable medical device are disclosed. One embodiment disclosed herein is a method for programming an implantable medical device (IMD) having a plurality of electrodes implantable in a patient. According to some embodiments the method comprises selecting a stimulation program defining a plurality of sequential pulses, wherein each pulse comprises a first phase having a first polarity and a second phase having a second polarity opposite of the first polarity, wherein the first and second phases are separated by an inter-phase interval (IPI). According to some embodiments, the method comprises applying the stimulation program using a plurality of differing IPIs, based on a determination of effectiveness of the stimulation program using the plurality of differing IPIs, determining a best IPI, and using the best IPI in programming the IMD. According to some embodiments, the determination of effectiveness of the stimulation program using the plurality of differing IPIs is based on patient feedback. According to some embodiments, the patient feedback comprises rankings of the stimulation program using the plurality of differing IPIs. According to some embodiments, the determination of effectiveness of the stimulation program using the plurality of differing IPIs is based on an electrospinogram (ESG) trace. According to some embodiments, the ESG trace is measured using one or more electrodes of the plurality of electrodes. According to some embodiments, the determination of effectiveness of the stimulation program using the plurality of differing IPIs based on an ESG trace comprises comparing ESG traces obtained using the stimulation program with each of the differing IPIs to a target ESG trace. According to some embodiments, the target ESG trace corresponds to stimulation settings that provide effective paresthesia coverage of the patient's pain. According to some embodiments, the target ESG trace corresponds to settings that provide effective pain relief without paresthesia. According to some embodiments, the target ESG trace is derived based on neural modeling predictions and/or one or more templates generated from previously recorded data. According to some embodiments, the method further comprises obtaining a target ESG using supra-perception stimulation and wherein the determination of the effectiveness of the stimulation program using the one or more differing IPIs comprises using sub-perception stimulation. According to some embodiments, the target ESG trace corresponds to stimulation that provides an effective temporal firing pattern of neural elements. According to some embodiments, the method further comprises determining the plurality of differing IPIs. According to some embodiments, determining the plurality of differing IPIs comprises predicting, based on neural modeling, temporal firing patterns of neural elements evoked by the differing IPIs. According to some embodiments, applying the stimulation program using the plurality of differing IPIs comprises using a graphical user interface (GUI) to select the plurality of differing IPIs. According to some embodiments, the GUI is configured to provide a ranking of the effectiveness of the stimulation program using each of the plurality of differing IPIs. According to some embodiments, the GUI is configured to provide an indication of an expected physiological and/or clinical effect associated with the stimulation program using the plurality of differing IPIs. According to some embodiments, the second phase is actively driven. According to some embodiments, the second phase is passively driven. According to some embodiments, the plurality differing IPIs are from 10 microseconds to 500 microseconds. According to some embodiments, the method further comprises determining a best stimulation geometry to produce a desired physiological effect. According to some embodiments, the best IPI is determined based on the determined best stimulation geometry. According to some embodiments, the plurality differing IPIs are from 0.5 µs to 2.5 µs.

A further embodiment disclosed herein is a method for programming an implantable medical device (IMD) having a plurality of electrodes implantable in a patient, wherein the method comprises selecting a stimulation program defining a plurality of sequential pulses, wherein each pulse comprises a first phase having a first polarity and a second phase having a second polarity opposite of the first polarity, wherein the first and second phases are separated by an inter-phase interval (IPI); selecting an IPI, wherein the selected IPI is predicted by neural modeling to produce a desired physiological and/or clinical effect; and using the selected IPI in programming the IMD. According to some embodiments, the neural modeling predicts temporal firing patterns of neural elements evoked by the effective IPI. According to some embodiments, the neural modeling predicts the effective IPI based on one or more parameters selected from the group consisting of stimulation geometry, pulse width, frequency, and amplitude. According to some embodiments, the method further comprises using a graphical user interface (GUI) to select the IPI. According to some embodiments, the GUI provides an indication of a predicted physiological and/or clinical effect for the effective IPI. According to some embodiments, the GUI provides a recommended range of IPIs.

Also disclosed herein is a neuromodulation system comprising: an external device for programming an implantable medical device (IMD), wherein the IMD comprises a plurality of electrodes implantable in a patient's tissue, and wherein the external device comprises a non-transitory computer readable medium comprising instructions, which when executed by the external device configures the external device to: select a stimulation program defining a plurality of sequential pulses, wherein each pulse comprises a first phase having a first polarity and a second phase having a second polarity opposite of the first polarity, wherein the first and second phases are separated by an inter-phase interval (IPI); enable the IMD to apply the stimulation program using a plurality of differing IPIs; based on a determination of effectiveness of the stimulation program using the differing IPIs, determine a best IPI; and use the best IPI in programming the IMD. According to some embodiments, the determination of effectiveness of the stimulation program using the plurality of differing IPIs is based on patient feedback. According to some embodiments, the patient feedback comprises rankings of the stimulation program using the plurality of differing IPIs. According to some embodiments, the determination of effectiveness of the stimulation program using the plurality of differing IPIs is based on an electrospinogram (ESG) trace. According to some embodiments, the ESG trace is measured using one or more electrodes of the plurality of electrodes. According to some embodiments, the determination of effectiveness of the stimulation program using the plurality of differing IPIs based on an ESG trace comprises comparing ESG traces obtained using the stimulation program with each of the differing IPIs to a target ESG trace. According to some embodiments, the target ESG trace corresponds to stimulation settings that provide effective paresthesia coverage of the patient's pain. According to some embodiments, the target ESG trace corresponds to settings that provide effective pain relief without paresthesia. According to some embodiments, the target ESG trace is derived based on neural modeling predictions and/or one or more templates generated from previously recorded data. According to some embodiments, the instructions further configure the external device to obtain a target ESG using supra-perception stimulation and wherein the determination of the effectiveness of the stimulation program using the one or more differing IPIs comprises using sub-perception stimulation. According to some embodiments, the target ESG trace corresponds to stimulation that provides an effective temporal firing pattern of neural elements. According to some embodiments, the instructions further configure the external device to determine the plurality of differing IPIs. According to some embodiments, determining the plurality of differing IPIs comprises predicting, based on neural modeling, temporal firing patterns of neural elements evoked by the differing IPIs. According to some embodiments, applying the stimulation program using the plurality of differing IPIs comprises using a graphical user interface (GUI) to select the plurality of differing IPIs. According to some embodiments, the GUI is configured to provide a ranking of the effectiveness of the stimulation program using each of the plurality of differing IPIs. According to some embodiments, the GUI is configured to provide an indication of an expected physiological and/or clinical effect associated with the stimulation program using the plurality of differing IPIs. According to some embodiments, the second phase is actively driven. According to some embodiments, the second phase is passively driven. According to some embodiments, the plurality differing IPIs are from 10 microseconds to 500 microseconds. According to some embodiments, the instructions further cause the external device to determine a best stimulation geometry to produce a desired physiological effect. According to some embodiments, the best IPI is determined based on the determined best stimulation geometry. According to some embodiments, the plurality differing IPIs are from 0.5 µs to 2.5 µs.

Also disclosed herein is a neuromodulation system comprising: an external device for programming an implantable medical device (IMD), wherein the IMD comprises a plurality of electrodes implantable in a patient's tissue, and wherein the external device comprises a non-transitory computer readable medium comprising instructions, which when executed by the external device configures the external device to: select a stimulation program defining a plurality of sequential pulses, wherein each pulse comprises a first phase having a first polarity and a second phase having a second polarity opposite of the first polarity, wherein the first and second phases are separated by an inter-phase interval (IPI); select an IPI, wherein the selected IPI is predicted by neural modeling to produce a desired physiological and/or clinical effect; and use the selected IPI in programming the IMD. According to some embodiments, the neural modeling predicts temporal firing patterns of neural elements evoked by the effective IPI. According to some embodiments, the neural modeling predicts the effective IPI based on one or more parameters selected from the group consisting of stimulation geometry, pulse width, frequency, and amplitude. According to some embodiments, the instructions further configure the external device to display a graphical user interface (GUI) for selecting the IPI. According to some embodiments, the GUI provides an indication of a predicted physiological and/or clinical effect for the effective IPI. According to some embodiments, the GUI provides a recommended range of IPIs.

Also disclosed herein is a non-transitory computer readable media comprising instructions executable on an external device for programming an implantable medical device (IMD), wherein the implantable medical device comprises a plurality of electrodes implantable in a patient's tissue, and wherein the computer readable media comprises instructions, which when executed, cause the external device to: select a stimulation program defining a plurality of sequential pulses, wherein each pulse comprises a first phase having a first polarity and a second phase having a second polarity opposite of the first polarity, wherein the first and second phases are separated by an inter-phase interval (IPI), enable the IMD to apply the stimulation program using a plurality of differing IPIs, based on a determination of effectiveness of the stimulation program using the differing IPIs, determine a best IPI; and use the best IPI in programming the IMD. According to some embodiments, the determination of effectiveness of the stimulation program using the plurality of differing IPIs is based on patient feedback. According to some embodiments, the patient feedback comprises rankings of the stimulation program using the plurality of differing IPIs. According to some embodiments, the determination of effectiveness of the stimulation program using the plurality of differing IPIs is based on an electrospinogram (ESG) trace. According to some embodiments, the ESG trace is measured using one or more electrodes of the plurality of electrodes. According to some embodiments, the determination of effectiveness of the stimulation program using the plurality of differing IPIs based on an ESG trace comprises comparing ESG traces obtained using the stimulation program with each of the differing IPIs to a target ESG trace. According to some embodiments, the target ESG trace corresponds to stimulation settings that provide effective paresthesia coverage of the patient's pain. According to some embodiments, the target ESG trace corresponds to settings that provide effective pain relief without paresthesia. According to some embodiments, the target ESG trace is derived based on neural modeling predictions and/or one or more templates generated from previously recorded data. According to some embodiments, the instructions further cause the external device to obtain a target ESG using supra-perception stimulation and wherein the determination of the effectiveness of the stimulation program using the one or more differing IPIs comprises using sub-perception stimulation. According to some embodiments, the target ESG trace corresponds to stimulation that provides an effective temporal firing pattern of neural elements. According to some embodiments, the instructions further cause the external device to determine the plurality of differing IPIs. According to some embodiments, determining the plurality of differing IPIs comprises predicting, based on neural modeling, temporal firing patterns of neural elements evoked by the differing IPIs. According to some embodiments, applying the stimulation program using the plurality of differing IPIs comprises using the graphical user interface (GUI) to select the plurality of differing IPIs. According to some embodiments, the GUI is configured to provide a ranking of the effectiveness of the stimulation program using each of the plurality of differing IPIs. According to some embodiments, the GUI is configured to provide an indication of an expected physiological and/or clinical effect associated with the stimulation program using the plurality of differing IPIs. According to some embodiments, the second phase is actively driven. According to some embodiments, the second phase is passively driven. According to some embodiments, the plurality differing IPIs are from 10 microseconds to 500 microseconds. According to some embodiments, the instructions further cause the external device to determine a best stimulation geometry to produce a desired physiological effect. According to some embodiments, the best IPI is determined based on the determined best stimulation geometry. According to some embodiments, the plurality differing IPIs are from 0.5 µs to 2.5 µs.

Also disclosed herein is a non-transitory computer readable media comprising instructions executable on an external device for programming an implantable medical device (IMD), wherein the implantable medical device comprises a plurality of electrodes implantable in a patient's tissue, and wherein the computer readable media comprises instructions, which when executed, cause the external device to: select a stimulation program defining a plurality of sequential pulses, wherein each pulse comprises a first phase having a first polarity and a second phase having a second polarity opposite of the first polarity, wherein the first and second phases are separated by an inter-phase interval (IPI); select an IPI, wherein the selected IPI is predicted by neural modeling to produce a desired physiological and/or clinical effect; and use the selected IPI in programming the IMD. According to some embodiments, the neural modeling predicts temporal firing patterns of neural elements evoked by the effective IPI. According to some embodiments, the neural modeling predicts the effective IPI based on one or more parameters selected from the group consisting of stimulation geometry, pulse width, frequency, and amplitude. According to some embodiments, the instructions further configure the external device to display a graphical user interface (GUI) for selecting the IPI. According to some embodiments, the GUI provides an indication of a predicted physiological and/or clinical effect for the effective IPI. According to some embodiments, the GUI provides a recommended range of IPIs.

BRIEF DESCRIPTION OF THE DRAWINGS

FIG. 1 shows an Implantable Pulse Generator (IPG) useable for Spinal Cord Stimulation (SCS).

FIG. 2 shows an example of stimulation pulses producible by the IPG.

FIG. 3 shows use of an External Trial Stimulator (ETS) useable to provide stimulation before implantation of an IPG.

FIGS. 6A-6D shows sweet spot searching to determine effective electrodes for a patient.

DETAILED DESCRIPTION

Figure 4:
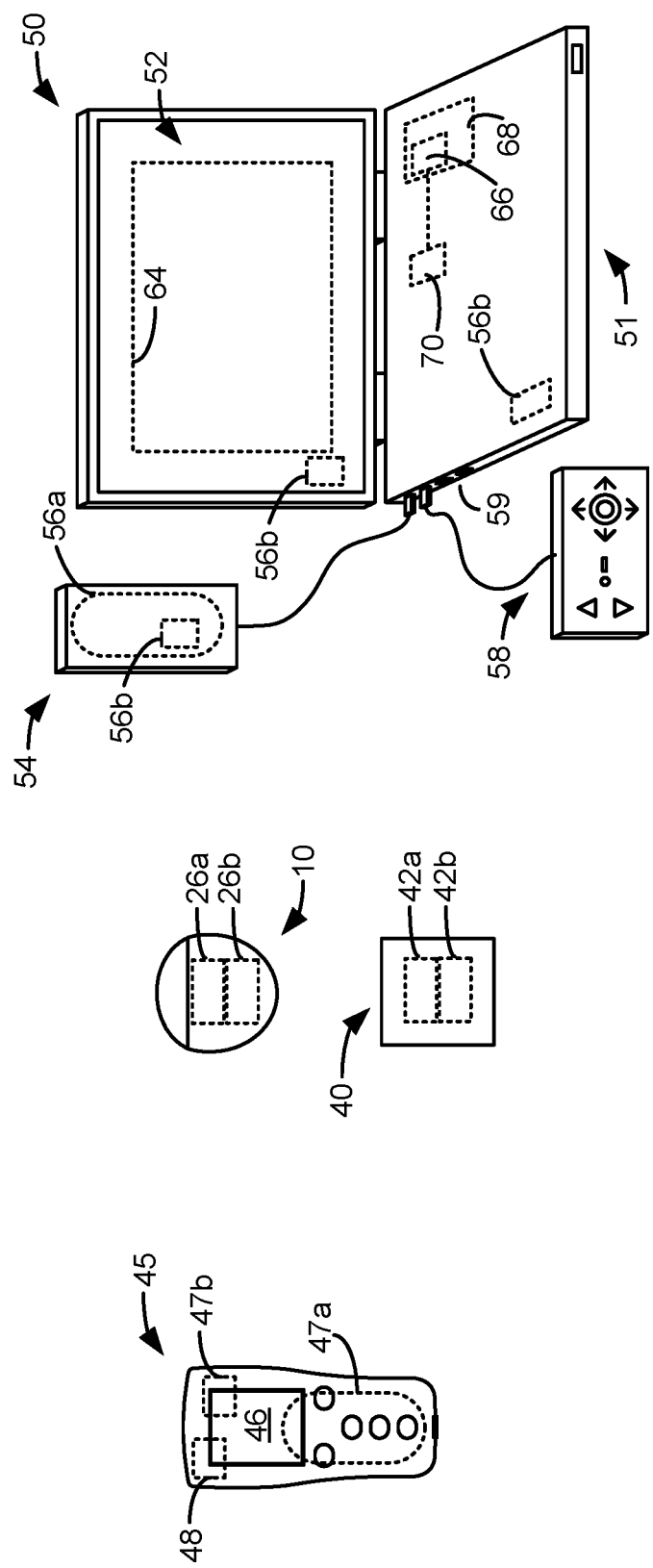
FIG. 4 shows various external devices capable of communicating with and programming stimulation in an IPG and ETS.

An SCS system typically includes an implantable medical device (IMD), more specifically, an Implantable Pulse Generator (IPG) 10 shown in FIG. 1. The IPG 10 includes a biocompatible device case 12 that holds the circuitry and battery 14 necessary for the IPG to function. The IPG 10 is coupled to electrodes 16 via one or more electrode leads 15 that form an electrode array 17. The electrodes 16 are configured to contact a patient's tissue and are carried on a flexible body 18, which also houses the individual lead wires 20 coupled to each electrode 16. The lead wires 20 are also coupled to proximal contacts 22, which are insertable into lead connectors 24 fixed in a header 23 on the IPG 10, which header can comprise an epoxy for example. Once inserted, the proximal contacts 22 connect to header contacts within the lead connectors 24, which are in turn coupled by feedthrough pins through a case feedthrough to circuitry within the case 12, although these details aren't shown.

In the illustrated IPG 10, there are sixteen lead electrodes (E1-E16) split between two leads 15, with the header 23 containing a 2×1 array of lead connectors 24. However, the number of leads and electrodes in an IPG is application specific and therefore can vary. The conductive case 12 can also comprise an electrode (Ec). In a SCS application, the electrode leads 15 are typically implanted proximate to the dura in a patient's spinal column on the right and left sides of the spinal cord midline. The proximal electrodes 22 are tunneled through the patient's tissue to a distant location such as the buttocks where the IPG case 12 is implanted, at which point they are coupled to the lead connectors 24. In other IPG examples designed for implantation directly at a site requiring stimulation, the IPG can be lead-less, having electrodes 16 instead appearing on the body of the IPG for contacting the patient's tissue. The IPG leads 15 can be integrated with and permanently connected the case 12 in other IPG solutions. The goal of SCS therapy is to provide electrical stimulation from the electrodes 16 to alleviate a patient's symptoms, most notably chronic back pain.

IPG 10 can include an antenna 26a allowing it to communicate bi-directionally with a number of external devices, as shown in FIG. 4. The antenna 26a as depicted in FIG. 1 is shown as a conductive coil within the case 12, although the coil antenna 26a can also appear in the header 23. When antenna 26a is configured as a coil, communication with external devices preferably occurs using near-field magnetic induction. IPG may also include a Radio-Frequency (RF) antenna 26b. In FIG. 1, RF antenna 26b is shown within the header 23, but it may also be within the case 12. RF antenna 26b may comprise a patch, slot, or wire, and may operate as a monopole or dipole. RF antenna 26b preferably communicates using far-field electromagnetic waves. RF antenna 26b may operate in accordance with any number of known RF communication standards, such as Bluetooth, Zigbee, WiFi, MICS, and the like.

Stimulation in IPG 10 is typically provided by pulses, as shown in FIG. 2. Stimulation parameters typically include the amplitude of the pulses (A; whether current or voltage); the frequency (F) and pulse width (PW) of the pulses; the electrodes 16 (E) activated to provide such stimulation; and the polarity (P) of such active electrodes, i.e., whether active electrodes are to act as anodes (that source current to the tissue) or cathodes (that sink current from the tissue). These stimulation parameters taken together comprise a stimulation program that the IPG 10 can execute to provide therapeutic stimulation to a patient.

In the example of FIG. 2, electrode E5 has been selected as an anode, and thus provides pulses which source a positive current of amplitude+A to the tissue. Electrode E4 has been selected as a cathode, and thus provides pulses which sink a corresponding negative current of amplitude −A from the tissue. This is an example of bipolar stimulation, in which only two lead-based electrodes are used to provide stimulation to the tissue (one anode, one cathode). However, more than one electrode may act as an anode at a given time, and more than one electrode may act as a cathode at a given time (e.g., tripole stimulation, quadripole stimulation, etc.).

The pulses as shown in FIG. 2 are biphasic, comprising a first phase 30a, followed quickly thereafter by a second phase 30b of opposite polarity. As is known, use of a biphasic pulse is useful in active charge recovery. For example, each electrodes' current path to the tissue may include a serially-connected DC-blocking capacitor, see, e.g., U.S. Patent Application Publication 2016/0144183, which will charge during the first phase 30a and discharged (be recovered) during the second phase 30b. In the example shown, the first and second phases 30a and 30b have the same duration and amplitude (although opposite polarities), which ensures the same amount of charge during both phases. However, the second phase 30b may also be charged balance with the first phase 30a if the integral of the amplitude and durations of the two phases are equal in magnitude, as is well known. The width of each pulse, PW, is defined here as the duration of first pulse phase 30a, although pulse width could also refer to the total duration of the first and second pulse phases 30a and 30b as well. Note that an interphase period (IPI) during which no stimulation is provided may be provided between the two phases 30a and 30b.

IPG 10 includes stimulation circuitry 28 that can be programmed to produce the stimulation pulses at the electrodes as defined by the stimulation program. Stimulation circuitry 28 can for example comprise the circuitry described in U.S. Patent Application Publication Nos. 2018/0071513 and 2018/048909, or described in U.S. Pat. Nos. 8,606,362 and 8,620,436. These references are incorporated herein by reference.

FIG. 3 shows an external trial stimulation environment that may precede implantation of an IPG 10 in a patient. During external trial stimulation, stimulation can be tried on a prospective implant patient without going so far as to implant the IPG 10. Instead, one or more trial leads 15' are implanted in the patient's tissue 32 at a target location 34, such as within the spinal column as explained earlier. The proximal ends of the trial lead(s) 15' exit an incision 36 and are connected to an External Trial Stimulator (ETS) 40. The ETS 40 generally mimics operation of the IPG 10, and thus can provide stimulation pulses to the patient's tissue as explained above. See, e.g., U.S. Pat. No. 9,259,574, disclosing a design for an ETS. The ETS 40 is generally worn externally by the patient for a short while (e.g., two weeks), which allows the patient and his clinician to experiment with different stimulation parameters to try and find a stimulation program that alleviates the patient's symptoms (e.g., pain). If external trial stimulation proves successful, trial lead(s) 15' are explanted, and a full IPG 10 and lead(s) 15 are implanted as described above; if unsuccessful, the trial lead(s) 15' are simply explanted.

Like the IPG 10, the ETS 40 can include one or more antennas to enable bi-directional communications with external devices, explained further with respect to FIG. 4. Such antennas can include a near-field magnetic-induction coil antenna 42a, and/or a far-field RF antenna 42b, as described earlier. ETS 40 may also include stimulation circuitry 44 able to form the stimulation pulses in accordance with a stimulation program, which circuitry may be similar to or comprise the same stimulation circuitry 28 present in the IPG 10. ETS 40 may also include a battery (not shown) for operational power.

FIG. 4 shows various external devices that can wirelessly communicate data with the IPG 10 and the ETS 40, including a patient, hand-held external controller 45, and a clinician programmer 50. Both of devices 45 and 50 can be used to send a stimulation program to the IPG 10 or ETS 40—that is, to program their stimulation circuitries 28 and 44 to produce pulses with a desired shape and timing described earlier. Both devices 45 and 50 may also be used to adjust one or more stimulation parameters of a stimulation program that the IPG 10 or ETS 40 is currently executing. Devices 45 and 50 may also receive information from the IPG 10 or ETS 40, such as various status information, etc.

External controller 45 can be as described in U.S. Patent Application Publication 2015/0080982 for example, and may comprise either a dedicated controller configured to work with the IPG 10. External controller 45 may also comprise a general purpose mobile electronics device such as a mobile phone which has been programmed with a Medical Device Application (MDA) allowing it to work as a wireless controller for the IPG 10 or ETS 40, as described in U.S. Patent Application Publication 2015/0231402. External controller 45 includes a user interface, including means for entering commands (e.g., buttons or icons) and a display 46. The external controller 45's user interface enables a patient to adjust stimulation parameters, although it may have limited functionality when compared to the more-powerful clinician programmer 50, described shortly.

The external controller 45 can have one or more antennas capable of communicating with the IPG 10 and ETS 40. For example, the external controller 45 can have a near-field magnetic-induction coil antenna 47a capable of wirelessly communicating with the coil antenna 26a or 42a in the IPG 10 or ETS 40. The external controller 45 can also have a far-field RF antenna 47b capable of wirelessly communicating with the RF antenna 26b or 42b in the IPG 10 or ETS 40.

The external controller 45 can also have control circuitry 48 such as a microprocessor, microcomputer, an FPGA, other digital logic structures, etc., which is capable of executing instructions an electronic device. Control circuitry 48 can for example receive patient adjustments to stimulation parameters and create a stimulation program to be wirelessly transmitted to the IPG 10 or ETS 40.

Clinician programmer 50 is described further in U.S. Patent Application Publication 2015/0360038, and is only briefly explained here. The clinician programmer 50 can comprise a computing device 51, such as a desktop, laptop, or notebook computer, a tablet, a mobile smart phone, a Personal Data Assistant (PDA)-type mobile computing device, etc. In FIG. 4, computing device 51 is shown as a laptop computer that includes typical computer user interface means such as a screen 52, a mouse, a keyboard, speakers, a stylus, a printer, etc., not all of which are shown for convenience. Also shown in FIG. 4 are accessory devices for the clinician programmer 50 that are usually specific to its operation as a stimulation controller, such as a communication "wand" 54, and a joystick 58, which are couplable to suitable ports on the computing device 51, such as USB ports 59 for example.

The antenna used in the clinician programmer 50 to communicate with the IPG 10 or ETS 40 can depend on the type of antennas included in those devices. If the patient's IPG 10 or ETS 40 includes a coil antenna 26a or 42a, wand 54 can likewise include a coil antenna 56a to establish near-filed magnetic-induction communications at small distances. In this instance, the wand 54 may be affixed in close proximity to the patient, such as by placing the wand 54 in a belt or holster wearable by the patient and proximate to the patient's IPG 10 or ETS 40.

If the IPG 10 or ETS 40 includes an RF antenna 26b or 42b, the wand 54, the computing device 51, or both, can likewise include an RF antenna 56b to establish communication with the IPG 10 or ETS 40 at larger distances. (Wand 54 may not be necessary in this circumstance). The clinician programmer 50 can also establish communication with other devices and networks, such as the Internet, either wirelessly or via a wired link provided at an Ethernet or network port.

To program stimulation programs or parameters for the IPG 10 or ETS 40, the clinician interfaces with a clinician programmer graphical user interface (GUI) 64 provided on the display 52 of the computing device 51. As one skilled in the art understands, the GUI 64 can be rendered by execution of clinician programmer software 66 on the computing device 51, which software may be stored in the device's non-volatile memory 68. One skilled in the art will additionally recognize that execution of the clinician programmer software 66 in the computing device 51 can be facilitated by control circuitry 70 such as a microprocessor, microcomputer, an FPGA, other digital logic structures, etc., which is capable of executing programs in a computing device. Such control circuitry 70, in addition to executing the clinician programmer software 66 and rendering the GUI 64, can also enable communications via antennas 56a or 56b to communicate stimulation parameters chosen through the GUI 64 to the patient's IPG 10.

Figure 5:
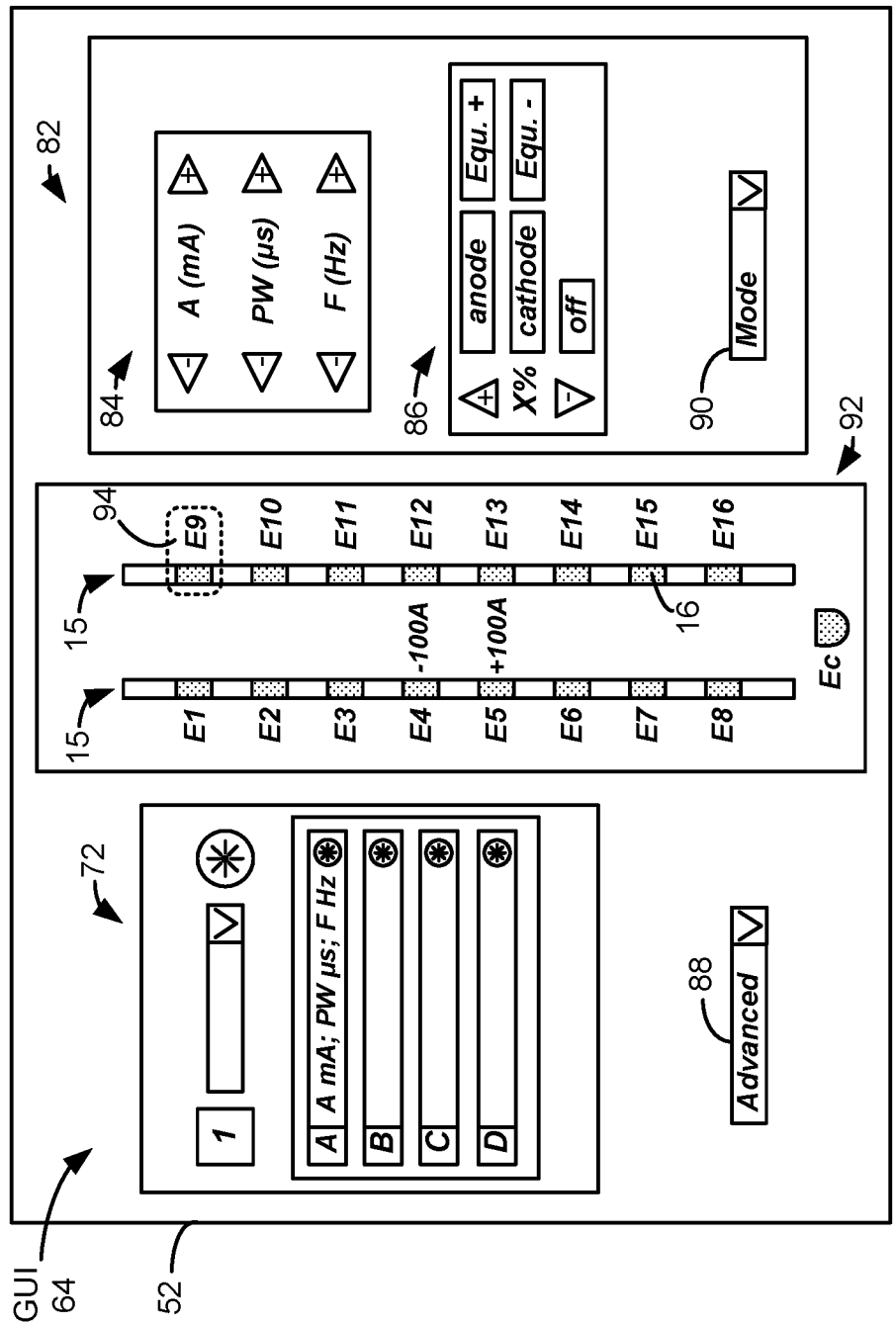
FIG. 5 shows a Graphical User Interface (GUI) of a clinician programmer external device for setting or adjusting stimulation parameters.

A portion of the GUI 64 is shown in one example in FIG. 5. One skilled in the art will understand that the particulars of the GUI 64 will depend on where clinician programmer software 66 is in its execution, which will depend on the GUI selections the clinician has made. FIG. 5 shows the GUI 64 at a point allowing for the setting of stimulation parameters for the patient and for their storage as a stimulation program. To the left a program interface 72 is shown, which as explained further in the '038 Publication allows for naming, loading and saving of stimulation programs for the patient. Shown to the right is a stimulation parameters interface 82, in which specific stimulation parameters (A, D, F, E, P) can be defined for a stimulation program. Values for stimulation parameters relating to the shape of the waveform (A; in this example, current), pulse width (PW), and frequency (F) are shown in a waveform parameter interface 84, including buttons the clinician can use to increase or decrease these values.

Stimulation parameters relating to the electrodes 16 (the electrodes E activated and their polarities P), are made adjustable in an electrode parameter interface 86. Electrode stimulation parameters are also visible and can be manipulated in a leads interface 92 that displays the leads 15 (or 15') in generally their proper position with respect to each other, for example, on the left and right sides of the spinal column. A cursor 94 (or other selection means such as a mouse pointer) can be used to select a particular electrode in the leads interface 92. Buttons in the electrode parameter interface 86 allow the selected electrode (including the case electrode, Ec) to be designated as an anode, a cathode, or off. The electrode parameter interface 86 further allows the relative strength of anodic or cathodic current of the selected electrode to be specified in terms of a percentage, X. This is particularly useful if more than one electrode is to act as an anode or cathode at a given time, as explained in the '038 Publication. In accordance with the example waveforms shown in FIG. 2, as shown in the leads interface 92, electrode E5 has been selected as the only anode to source current, and this electrode receives X=100% of the specified anodic current, +A. Likewise, electrode E4 has been selected as the only cathode to sink current, and this electrode receives X=100% of that cathodic current, −A.

The GUI 64 as shown specifies only a pulse width PW of the first pulse phase 30a. The clinician programmer software 66 that runs and receives input from the GUI 64 will nonetheless ensure that the IPG 10 and ETS 40 are programmed to render the stimulation program as biphasic pulses if biphasic pulses are to be used. For example, the clinician programming software 66 can automatically determine durations and amplitudes for both of the pulse phases 30a and 30b (e.g., each having a duration of PW, and with opposite polarities+A and −A). An advanced menu 88 can also be used (among other things) to define the relative durations and amplitudes of the pulse phases 30a and 30b, and to allow for other more advance modifications, such as setting of a duty cycle (on/off time) for the stimulation pulses, and a ramp-up time over which stimulation reaches its programmed amplitude (A), etc. A mode menu 90 allows the clinician to choose different modes for determining stimulation parameters. For example, as described in the '038 Publication, mode menu 90 can be used to enable electronic trolling, which comprises an automated programming mode that performs current steering along the electrode array by moving the cathode in a bipolar fashion. While GUI 64 is shown as operating in the clinician programmer 50, the user interface of the external controller 45 may provide similar functionality.

While Spinal Cord Stimulation (SC S) therapy can be an effective means of alleviating a patient's pain, such stimulation can also cause paresthesia. Paresthesia—sometimes referred to a "supra-perception" therapy—is a sensation such as tingling, prickling, heat, cold, etc. that can accompany SCS therapy. Generally, the effects of paresthesia are mild, or at least are not overly concerning to a patient. Moreover, paresthesia is generally a reasonable tradeoff for a patient whose chronic pain has now been brought under control by SCS therapy. Some patients even find paresthesia comfortable and soothing.

Nonetheless, at least for some patients, SCS therapy would ideally provide complete pain relief without paresthesia—what is often referred to as "sub-perception" or sub-threshold therapy that a patient cannot feel. Effective sub-perception therapy may provide pain relief without paresthesia by issuing stimulation pulses at higher frequencies. Unfortunately, such higher-frequency stimulation may require more power, which tends to drain the battery 14 of the IPG 10. See, e.g., U.S. Patent Application Publication 2016/0367822. If an IPG's battery 14 is a primary cell and not rechargeable, high-frequency stimulation means that the IPG 10 will need to be replaced more quickly. Alternatively, if an IPG battery 14 is rechargeable, the IPG 10 will need to be charged more frequently, or for longer periods of time. Either way, the patient is inconvenienced.

In an SCS application, it is desirable to determine a stimulation program that will be effective for each patient. A significant part of determining an effective stimulation program is to determine a "sweet spot" for stimulation in each patient, i.e., to select which electrodes should be active (E) and with what polarities (P) and relative amplitudes (X %) to recruit and thus treat a neural site at which pain originates in a patient. Selecting electrodes proximate to this neural site of pain can be difficult to determine, and experimentation is typically undertaken to select the best combination of electrodes to provide a patient's therapy.

As described in U.S. Patent Application Publication Nos. 2019/0366104 and 2019/0046800, both of which are hereby expressly incorporated by reference, selecting electrodes for a given patient can be even more difficult when sub-perception therapy is used, because the patient does not feel the stimulation, and therefore it can be difficult for the patient to feel whether the stimulation is "covering" his pain and therefore whether selected electrodes are effective. Further, sub-perception stimulation therapy may require a "wash in" period before it can become effective. A wash in period can take up to a day or more, and therefore sub-perception stimulation may not be immediately effective, making electrode selection more difficult.

The referenced '539 and '904 Applications disclose techniques for a sweet spot search which can be used with sub-perception therapy. In particular, the '904 Application describes techniques which use supra-perception stimulation during the sweet spot search to select active electrodes for the patient. Use of supra-perception stimulation during the sweet spot search greatly accelerates determination of effective electrodes for the patient compared to the use of sub-perception stimulation, which requires a wash in period at each set of electrodes tested. After determining electrodes for use with the patient using supra-perception therapy, therapy may be titrated to sub-perception levels keeping the same electrodes determined for the patient during the sweet spot search. Because the selected electrodes are known to be recruiting the neural site of the patient's pain, the application of sub-perception therapy to those electrodes is more likely to have immediate effect, reducing or potentially eliminating the need to wash in the sub-perception therapy that follows. In short, effective sub-perception therapy can be achieved more quickly for the patient when supra-perception sweet spot searching is utilized. According to some embodiments, supra-perception sweet spot searching occurs using symmetric biphasic pulses occurring at low frequencies—such as between 40 and 200 Hz in one example.

Figure 6A:
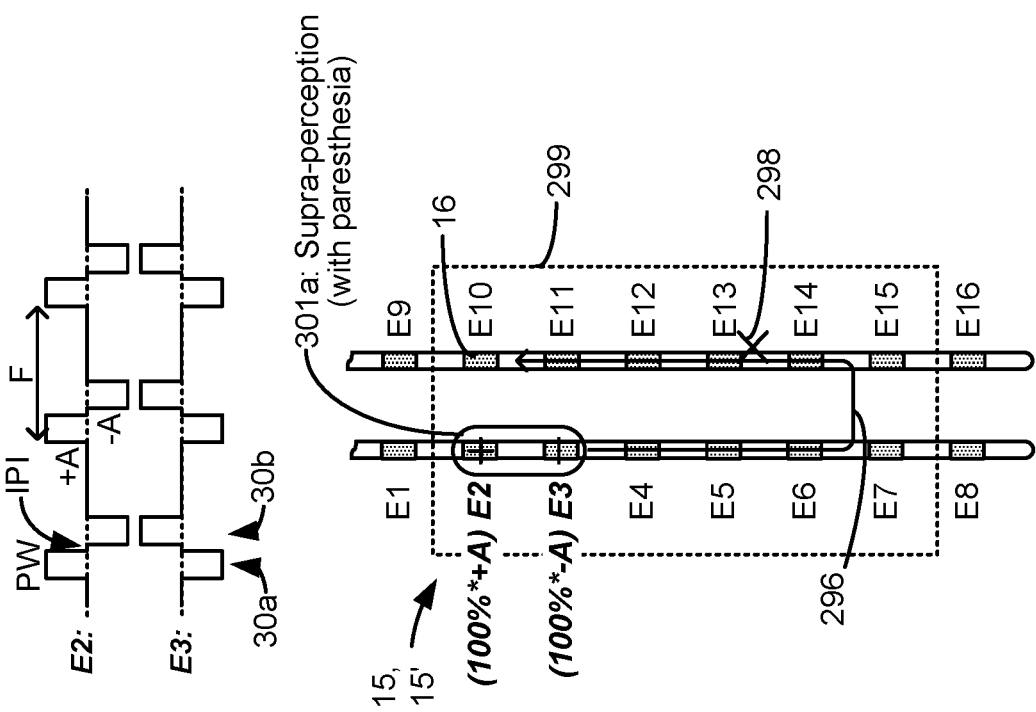
Figure 6B:
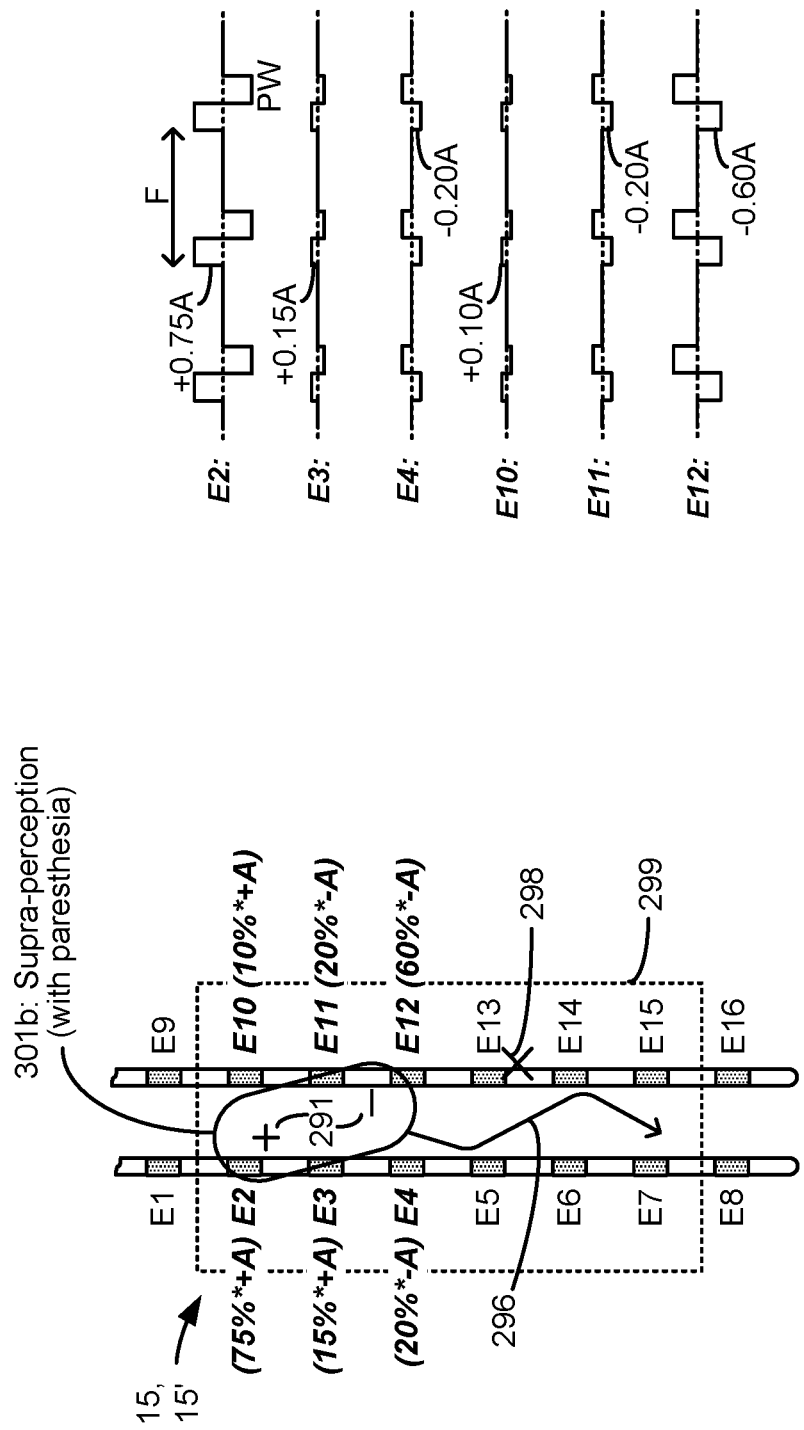
Figure 7A:
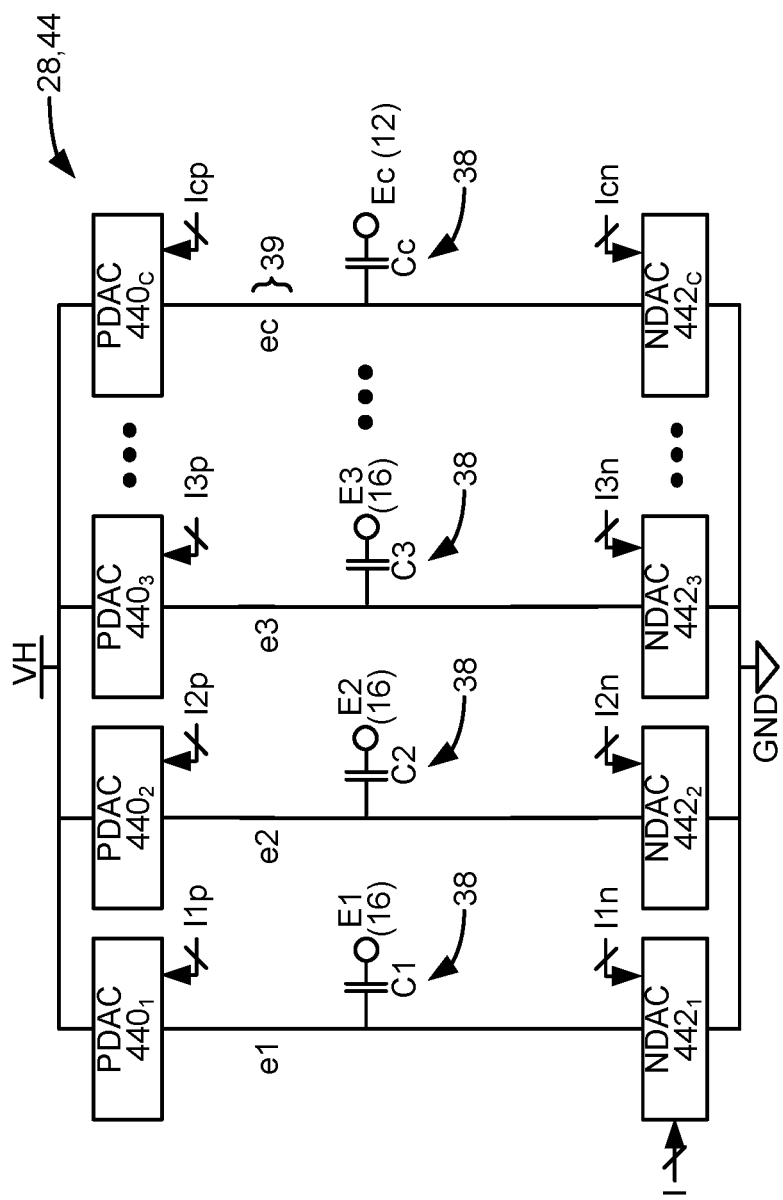
FIGS. 7A-7B show aspects of stimulation circuitry useable in the IPG or ETS.

This is shown in FIG. 6A, where the movable bipole 301a provides supra-perception stimulation that can be felt by the patient. Providing bipole 301a as supra-perception stimulation can merely involve increasing its amplitude (e.g., current A), although other stimulation parameters might be adjusted as well, such as by providing longer pulse widths. FIGS. 6B-6D show other supra-perception bipoles 301b-301d that may be used, and in particular show how the virtual bipoles may be formed using virtual poles by activating three or more of the electrodes 16. Virtual poles are discussed further in U.S. patent application Publication 2019/0175915, which is incorporated herein by reference in its entirety, and thus virtual poles are only briefly explained here. Forming virtual poles is assisted if the stimulation circuitry 28 or 44 used in the IPG or ETS is capable of independently setting the current at any of the electrodes-what is sometimes known as a Multiple Independent Current Control (MICC), which is explained further below with reference to FIG. 7.

When a virtual bipole is used, the GUI 64 (FIG. 5) of the clinician programmer 50 (FIG. 4) can be used to define an anode pole (+) and a cathode pole (−) at positions 291 (FIG. 6B) that may not necessarily correspond to the position of the physical electrodes 16. The control circuitry 70 in the clinician programmer 50 can compute from these positions 291 and from other tissue modeling information which physical electrodes 16 will need to be selected and with what amplitudes to form the virtual anode and virtual cathode at the designated positions 291. As described earlier, amplitudes at selected electrodes may be expressed as a percentage X % of the total current amplitude A specified at the GUI 64 of the clinician programmer 50.

For example, in FIG. 6B, the virtual anode pole is located at a position 291 between electrodes E2, E3 and E10. The clinician programmer 50 may then calculate based on this position that each of these electrodes (during first pulse phase 30a) will receive an appropriate share (X %) of the total anodic current+A to locate the virtual anode at this position. Since the virtual anode's position is closest to electrode E2, this electrode E2 may receive the largest share of the specified anodic current+A (e.g., 75%*+A). Electrodes E3 and E10 which are proximate to the virtual anode pole's position but farther away receive lesser shares of the anodic current (e.g., 15%*+A and 10%*+A respectively). Likewise, it can be seen that from the designated position 291 of the virtual cathode pole, which is proximate to electrodes E4, E11, and E12, that these electrodes will receive an appropriate share of the specified cathodic current—A (e.g., 20%*–A, 20%*–A, and 60%*–A respectively, again during the first pulse phase 30a). These polarities would then be flipped during the second phases 30b of the pulses, as shown in the waveforms of FIG. 6B. In any event, the use of virtual poles in the formation of bipole 301b allows the field in the tissue to be shaped, and many different combinations of electrodes can be tried during the sweet spot search. In this regard, it is not strictly necessary that the (virtual) bipole be moved along an orderly path 296 with respect to the electrodes, and the path may be randomized, perhaps as guided by feedback from the patient.

FIG. 6C shows a useful virtual bipole 301c configuration that can be used during the sweet spot search. This virtual bipole 301c again defines a target anode and cathode whose positions do not correspond to the position of the physical electrodes. The virtual bipole 301c is formed along a lead—essentially spanning the length of four electrodes from E1 to E5. This creates a larger field in the tissue better able to recruit the patient's pain site 298. This bipole configuration 301c may need to be moved to a smaller number of locations than would a smaller bipole configuration compared 301a of FIG. 6A) as it moves along path 296, thus accelerating pain site 298 detection. FIG. 6D expands upon the bipole configuration of FIG. 6C to create a virtual bipole 301d using electrodes formed on both leads, e.g., from electrodes E1 to E5 and from electrodes E9 to E13. This bipole 301d configuration need only be moved along a single path 296 that is parallel to the leads, as its field is large enough to recruit neural tissue proximate to both leads. This can further accelerate pain site detection.

As mentioned above, forming virtual poles is assisted if the stimulation circuitry 28 or 44 used in the IPG or ETS is capable of independently setting the current at any of the electrodes—what is sometimes known as a Multiple Independent Current Control (MICC). Multiple Independent Current Control (MICC) is explained in one example with reference to FIG. 7A, which shows the stimulation circuitry 28 (FIG. 1) or 44 (FIG. 3) in the IPG or ETS used to form prescribed stimulation at a patient's tissue. The stimulation circuitry 28 or 44 can control the current or charge at each electrode independently, and using GUI 64 (FIG. 5) allows the current or charge to be steered to different electrodes, which is useful for example when moving the bipole 301i along path 296 during the sweet spot search (FIG. 6A-6D). The stimulation circuitry 28 or 44 includes one or more current sources $440_i$ and one or more current sinks $442_i$. The sources and sinks $440_i$ and $442_i$ can comprise Digital-to-Analog converters (DACs), and may be referred to as PDACs $440_i$ and NDACs $442_i$ in accordance with the Positive (sourced, anodic) and Negative (sunk, cathodic) currents they respectively issue. In the example shown, a NDAC/PDAC $440_i/442_i$ pair is dedicated (hardwired) to a particular electrode node ei 39. Each electrode node ei 39 is preferably connected to an electrode Ei 16 via a DC-blocking capacitor Ci 38, which act as a safety measure to prevent DC current injection into the patient, as could occur for example if there is a circuit fault in the stimulation circuitry 28 or 44. PDACs $440_i$ and NDACs $442_i$ can also comprise voltage sources.

Proper control of the PDACs $440_i$ and NDACs $442_i$ via GUI 64 allows any of the electrodes 16 and the case electrode Ec 12 to act as anodes or cathodes to create a current through a patient's tissue. Such control preferably comes in the form of digital signals Iip and Iin that set the anodic and cathodic current at each electrode Ei. If for example it is desired to set electrode E1 as an anode with a current of +3 mA, and to set electrodes E2 and E3 as cathodes with a current of –1.5 mA each, control signal I1p would be set to the digital equivalent of 3 mA to cause PDAC $440_1$ to produce+3 mA, and control signals I2n and I3n would be set to the digital equivalent of 1.5 mA to cause NDACs $442_2$ and $442_3$ to each produce—1.5 mA. Note that definition of these control signals can also occur using the programmed amplitude A and percentage X % set in the GUI 64. For example, A may be set to 3 mA, with E1 designated as an anode with X=100%, and with E2 and E3 designated at cathodes with X=50%. Alternatively, the control signals may not be set with a percentage, and instead the GUI 64 can simply prescribe the current that will appear at each electrode at any point in time.

In short, the GUI 64 may be used to independently set the current at each electrode, or to steer the current between different electrodes. This is particularly useful in forming virtual bipoles, which as explained earlier involve activation of more than two electrodes. MICC also allows more sophisticated electric fields to be formed in the patient's tissue.

Other stimulation circuitries 28 can also be used to implement MICC. In an example not shown, a switching matrix can intervene between the one or more PDACs $440_i$ and the electrode nodes ei 39, and between the one or more NDACs $442_i$ and the electrode nodes. Switching matrices allows one or more of the PDACs or one or more of the NDACs to be connected to one or more electrode nodes at a given time. Various examples of stimulation circuitries can be found in U.S. Pat. Nos. 6,181,969, 8,606,362, 8,620,436, U.S. Patent Application Publication Nos. 2018/0071513, 2018/0071520, and 2019/0083796.

Much of the stimulation circuitry 28 or 44, including the PDACs $440_i$ and NDACs $442_i$, the switch matrices (if present), and the electrode nodes ei 39 can be integrated on one or more Application Specific Integrated Circuits (ASICs), as described in U.S. Patent Application Publications 2012/0095529, 2012/0092031, and 2012/0095519. As explained in these references, ASIC(s) may also contain other circuitry useful in the IPG 10, such as telemetry circuitry (for interfacing off chip with the IPG's or ETS's telemetry antennas), circuitry for generating the compliance voltage VH that powers the stimulation circuitry, various measurement circuits, etc.

Figure 7B:
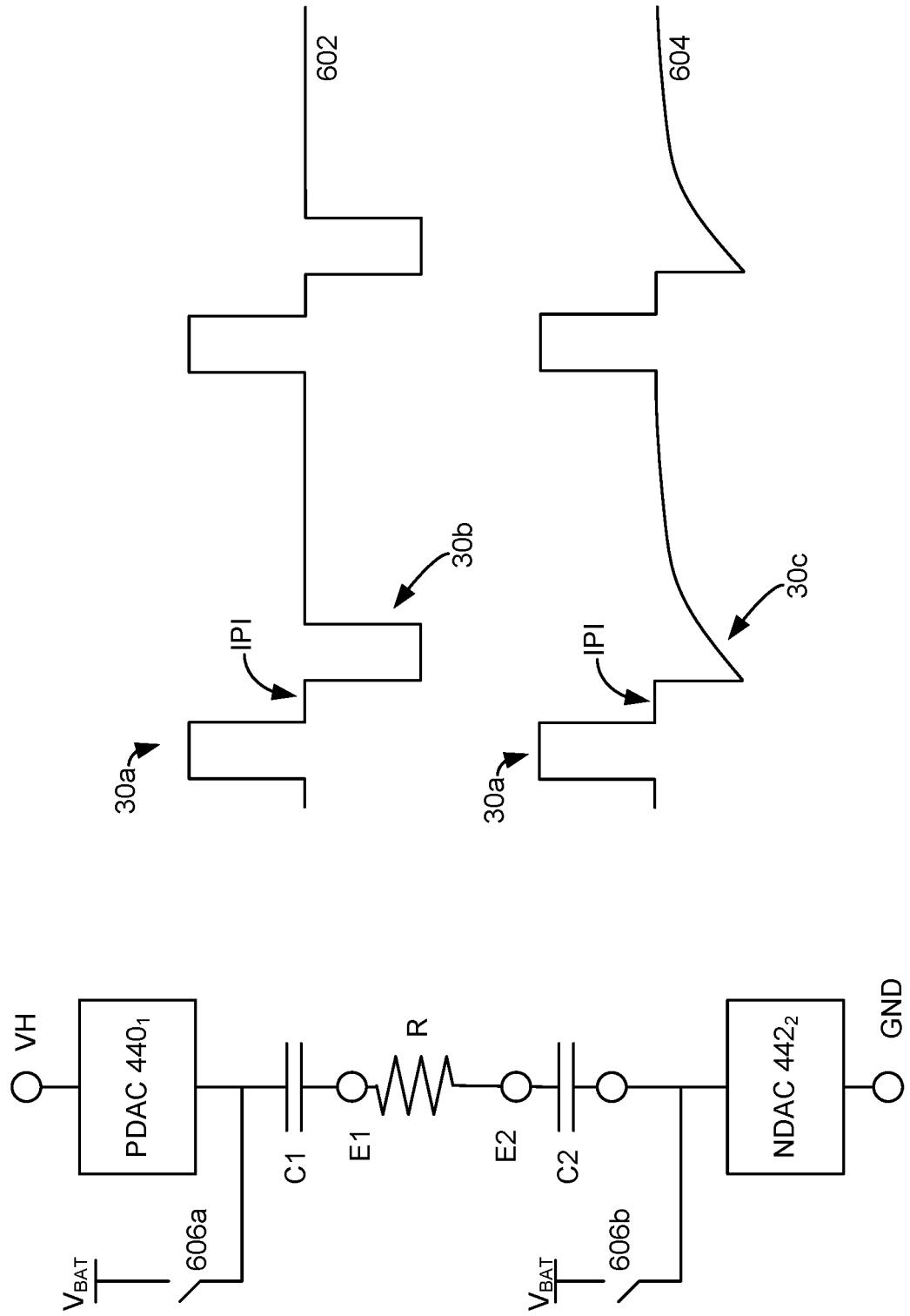

FIG. 7B illustrates the use of the stimulation circuitry 28 or 44 for making biphasic pulses. In the illustration, electrodes E1 and E2 and their corresponding PDACs and NDACs are active. The current passed via the electrodes complete a circuit through the tissue (represented by resistance R). Biphasic waveform 602 comprising a first phase 30a, followed quickly thereafter by a second phase 30b of opposite polarity and having an interphase interval (IPI). As mentioned above, use of a biphasic pulse is useful in charge recovery. The waveform 602 is an example of active charge recovery, meaning that both the first phase 30a and second phase 30b are actively driven. However, it should be noted that passive charge recovery can also be used. Waveform

604 is an example of passive charge recovery. In the waveform 604, the first phase 30a is actively driven. The second phase 30c is passively driven by closing switches 606a and 606b, which effectively shorts the capacitors C1 and C2 to the battery voltage VBAT. Thus, embodiments of the disclosure discussed below deal with waveforms (i.e., sequences of pulses) comprising pulses, wherein the pulses have a first phase of a first polarity and a second phase of a second polarity opposite the first polarity. The second phases may be either actively or passively driven.

Figure 8:
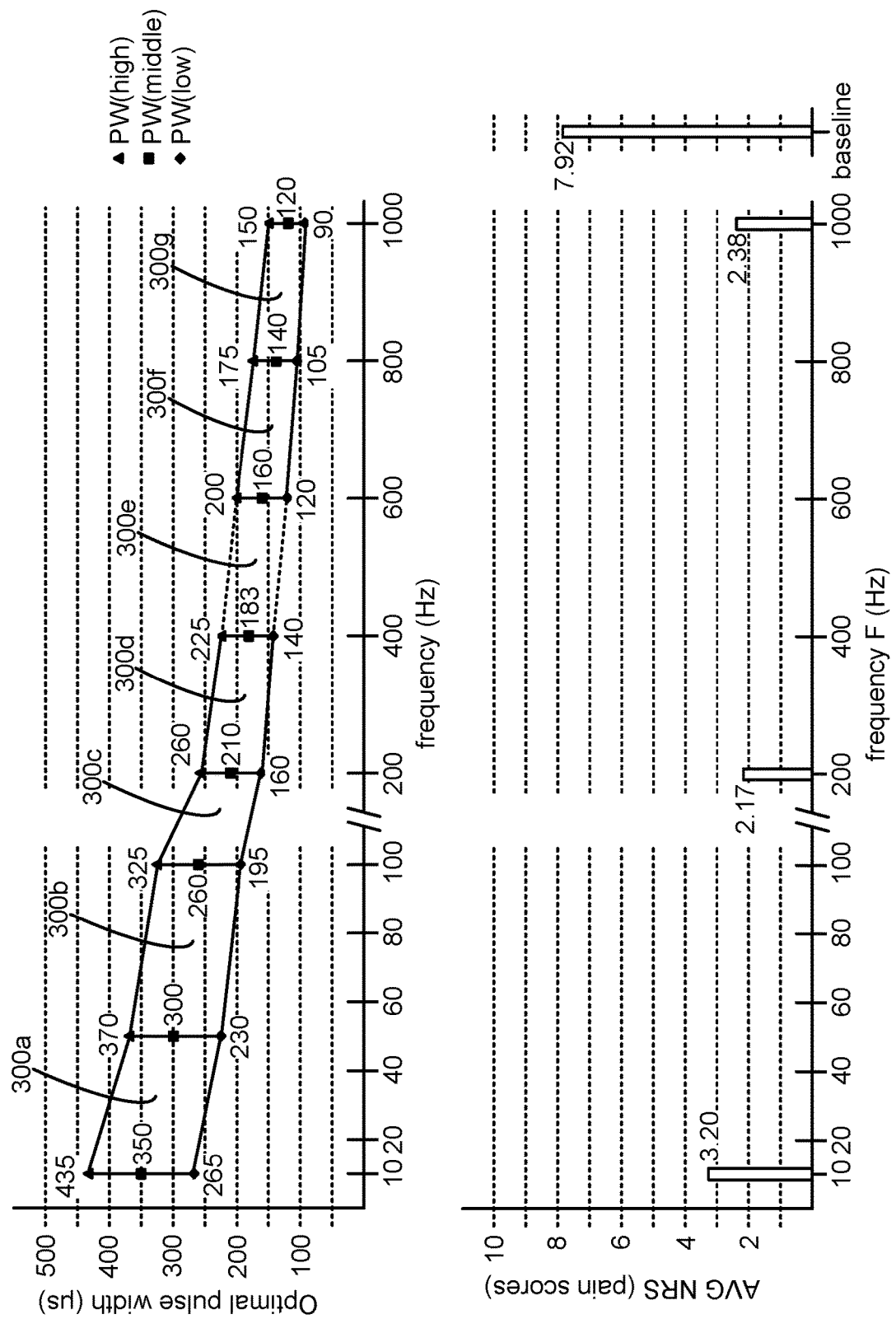
FIG. 8 shows results of patients tested with sub-perception therapy at frequencies at or below 1 kHz, and shows optimal pulse width ranges determined at tested frequencies, and optimal pulse width v. frequency regions for sub-perception therapy.

The '904 Application also discloses that statistically significant correlations exists between pulse width (PW) and frequency (F) where an SCS patient will experience a reduction in pain without paresthesia (sub-perception). For example, FIG. 8 shows the relationship between frequency and pulse width at which effective sub-perception therapy was reported by patients for frequencies of 1 kHz and below. As can be seen, at each frequency tested, the optimal pulse width again fell within a range. For example, at 800 Hz, patients reported good results when the pulse width fell within a range of 105-175 microseconds. The upper end of the pulse width range at each frequency is denoted PW(high), while the lower end of the pulse width range at each frequency is denoted PW(low). PW(middle) denotes the middle (e.g., average) of the PW(high) and PW(low) at each frequency. At each of the tested frequencies the amplitude of the current provided (A) was titrated down to sub-perception levels, such that the patient could not feel paresthesia. Typically, the current was titrated to 80% of the threshold at which paresthesia could be sensed. Because each patient's anatomy is unique, the sub-perception amplitude A could vary from patient to patient. The pulse width data depicted comprises the pulse width of only the first phase of the stimulation pulses. The data may be broken down to define different regions 300i at which effective sub-perception therapy is realized below 1 kHz. For example, regions of effective sub-perception therapy may be linearly bounded between various frequencies and the high and low pulse widths that define effectiveness. For example, at 10 Hz, PW(low)=265 microseconds and PW(high)=435 microseconds. At 50 Hz, PW(low)=230 microseconds and PW(high)=370 microseconds. Therefore, a region 300a that provides good sub-perception therapy is defined by the linearly bounded region of points (10 Hz, 265 µs), (10 Hz, 435 µs), (50 Hz, 370 µs), and (50 Hz, 230 µs). Also shown in FIG. 8 are average patient pain scores (NRS scores) reported by patients when optimal pulse widths are used for different frequencies at 1 kHz or below. Prior to receiving SCS therapy, patients initially reported pain scores with an average of 7.92. After SCS implantation, and using the sub-perception stimulation at optimal pulse widths with the ranges shown at each frequency, the patients' average pain scores dropped significantly. At 1 kHz, 200 Hz, and 10 Hz, patients reported average pain scores of 2.38, 2.17, and 3.20 respectively. Thus, clinical significance with respect to pain relief is shown when the optimal pulse widths are used at or below 1 kHz with sub-perception therapy.

Use of this information can be helpful in deciding what pulse width is likely optimal for a given SCS patient based on a particular frequency, and in deciding what frequency is likely optimal for a given SCS patient based on a particular pulse width. Beneficially, this information suggests that paresthesia-free sub-perception SCS stimulation can occur at frequencies of 10 kHz and below, as well as 1 kHz and below. Use of such low frequencies allows sub-perception therapy to be used with much lower power consumption in the patient's IPG or ETS.

The inventors have discovered that stimulation geometry and waveform properties such as the interphase interval (IPI), pulse width, and duty cycle may interact with frequency and stimulation amplitude to produce physiological effects. Thus, aspects of the present disclosure provide methods and systems to control such parameters.

Figure 9A:
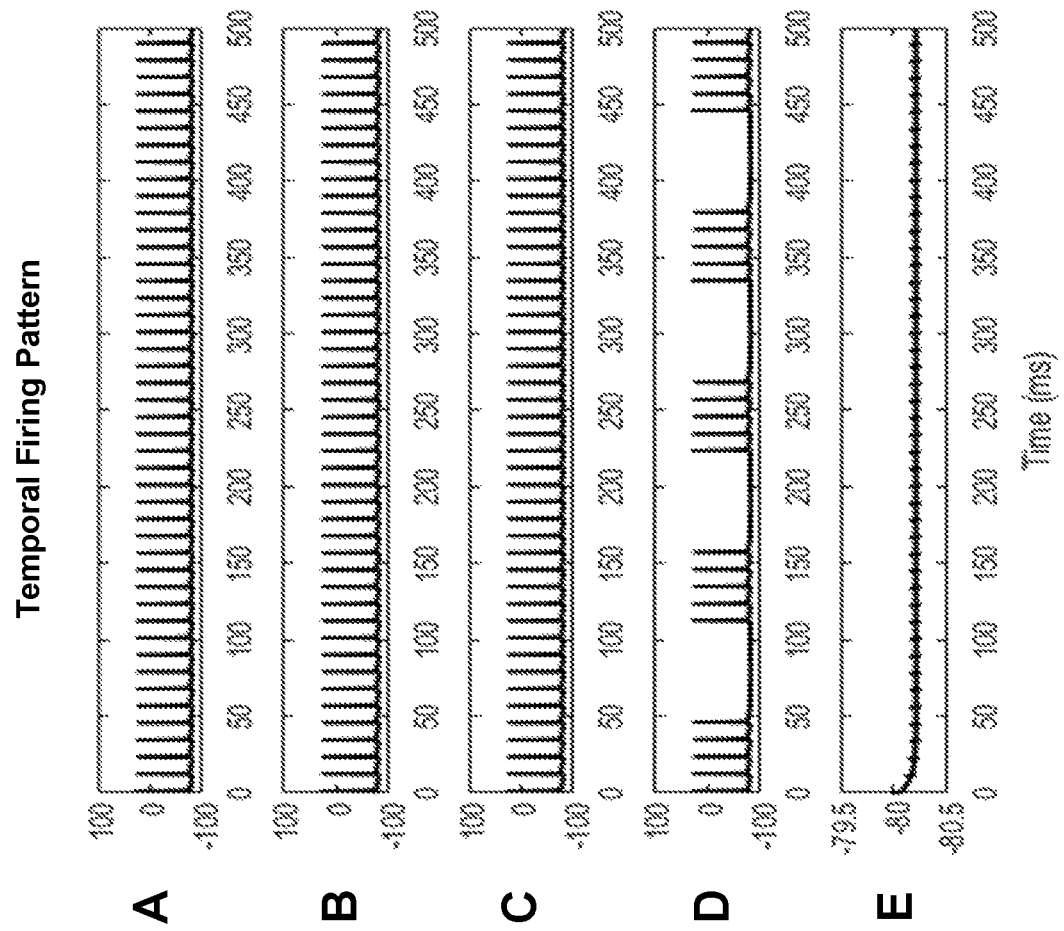
FIGS. 9A-9C show temporal firing patterns of neural elements using differing stimulation parameters.
Figure 9A:
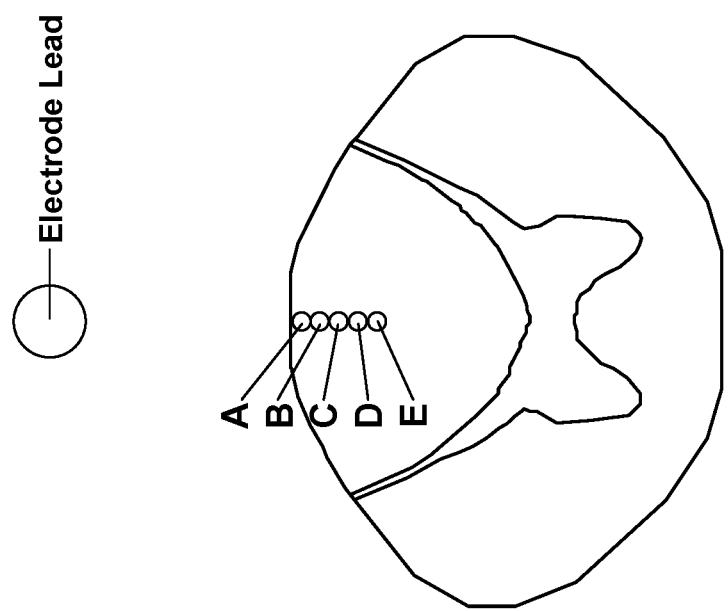
Figures 9B, 9C:
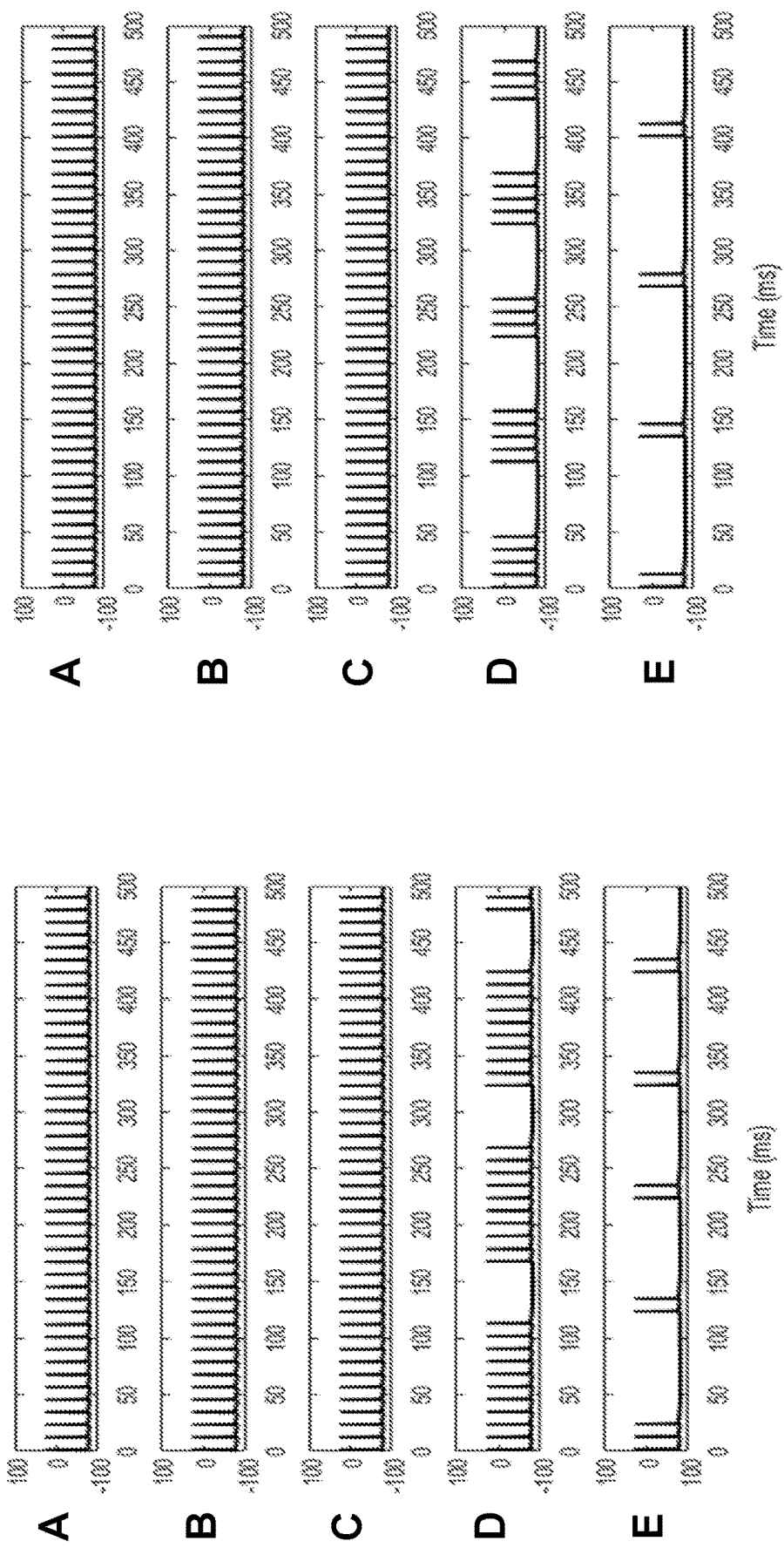

FIGS. 9A-9C illustrate how changes in stimulation geometry and waveform properties such as IPI affect the temporal firing patterns of dorsal column fibers. FIG. 9A shows computational modeling assuming a dorsal cerebral spinal fluid thickness (dCSF) of 3.2 mm, 90 Hz bipolar stimulation with a pulse width of 300 µs (300 µs for each phase), with a bipole distance of 8 mm (meaning that the anode and cathode contacts are separated by 8 mm), and an IPI of 50 µs. Temporal firing patterns of dorsal column (DC) fibers at depths A-E were modeled. As shown, firing of fibers at depths A-C are essentially synchronous with the stimulation frequency, that is, they fire each time a stimulus pulse is applied. However, fibers at depth D fire in a pattern that is asynchronous with respect to the stimulation frequency, i.e., they do not fire each time a stimulation pulse is applied. Fibers at depth E are not activated under the stimulation conditions.

FIG. 9B illustrates the temporal firing patterns of fibers at depths A-E when the IPI is changed to 200 µs. Again, fibers at depths A-C fire essentially synchronous with the stimulation frequency. But notice that the firing pattern of the depth D fibers is changed compared to the pattern of the depth D fibers of FIG. 9A. Moreover, stimulation the waveform with an IPI of 200 µs (FIG. 9B) activates the fibers at depth E, whereas the waveform with an IPI of 50 µs does not (FIG. 9A). FIG. 9C illustrates the temporal firing patterns of fibers at depths A-E using a 12 mm bipole (as opposed to the 8 mm bipole used in FIGS. 9A and 9B). Again, the temporal firing pattern of the fibers at depths D and E are affected.

The data illustrated in FIGS. 9A-9C show that stimulation parameters such as IPI, frequency, pulse width, and amplitude, as well as stimulation geometry parameters such as pole configuration (i.e., bipole, tripole, length of pole configuration, etc.) and electrode configuration, may interact with each other to influence temporal fiber activation. Those differences can also affect therapy and side effects.

Thus, aspects of the disclosure provide methods and systems for delivering user-configured waveforms with different IPIs, stimulation geometry, and other waveform settings (e.g., pulse width, frequency, amplitude) and pain etiology to induce therapeutic asynchronous activation of the neural tissues. Aspects of the disclosure allow a clinician to select and evaluate IPIs based on stimulation settings such as stimulation geometry and other waveform parameters. Stimulation geometry, polarity, IPI and other settings can be selected to induce or maintain temporal firing patterns that are known or calculated to correspond to desirable therapeutic outcomes. Parameter selection can be based on patient feedback and/or expected effects. For example, according to some embodiments described below, stimulation programs using stimulation parameters and stimulation geometries are evaluated using different IPIs to determine optimal/desired temporal neural activation to correlate with desired physiological and/or clinical effects. Other embodiments utilize neural modeling to predict the interaction of different IPIs with stimulation parameters and/or stimulation geometries to predict optimal/desired temporal neural activation, which may be correlated with desired physiological and/or clinical effects. Examples of modeling neural fiber activation are described, for example, in U.S. Patent Application Publication No. 2018/0064943; "Computational Analysis of Kilohertz Frequency Spinal Cord stimulation for Chronic Pain Management," S. Lempka, et al., Anesthesiology, 122, 6, 2015, 1362-76; and Spinal Sensory Projection Neuron Responses to Spinal Cord Stimulation are Mediated by Circuits Beyond Gate Control," T. Zhang, et. al., J. Neurophysiol. 114, 1, 2015, 284-300, and the references cited therein.

Figure 10:
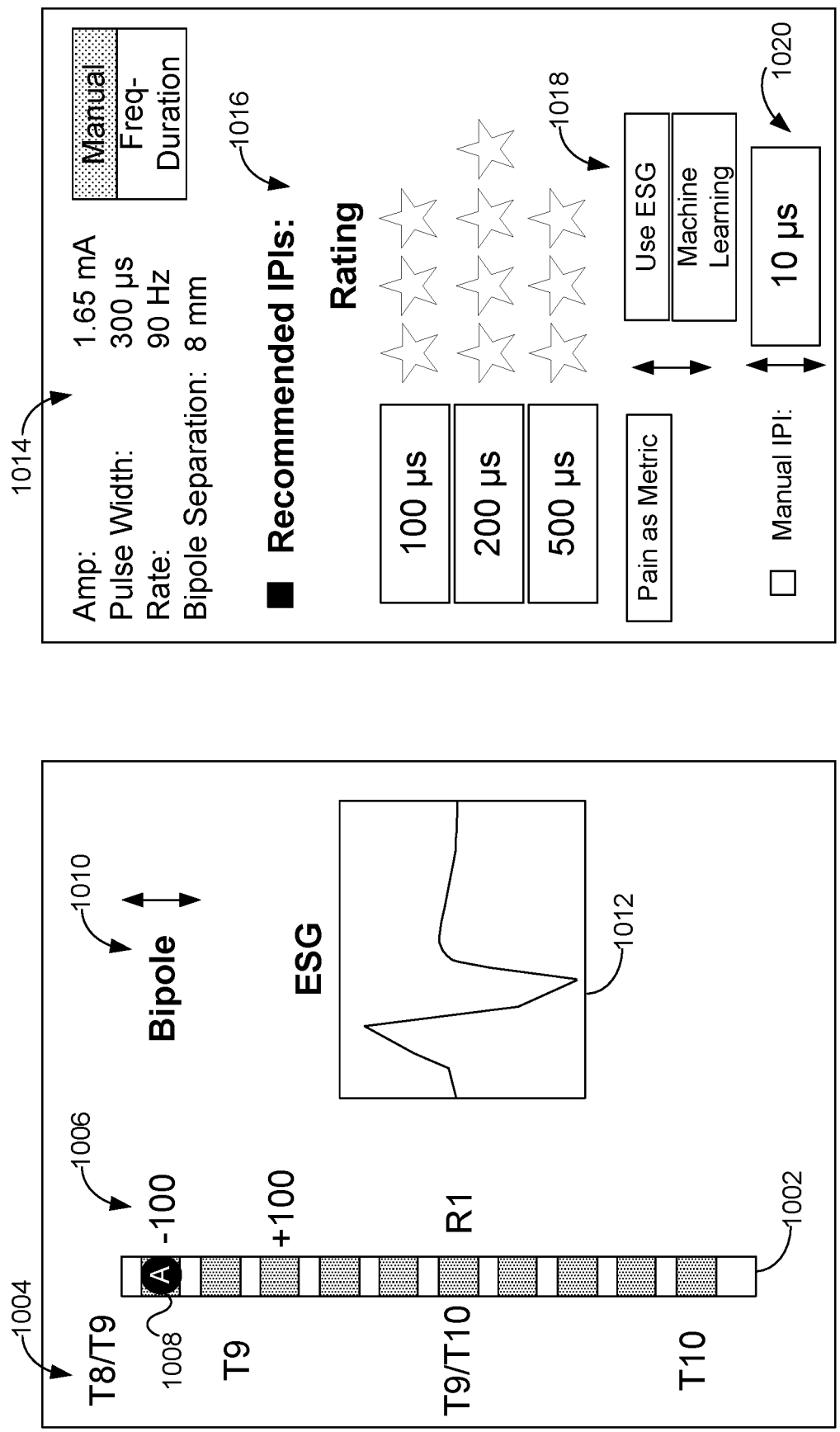
FIG. 10 shows an embodiment of a GUI for optimizing interphase intervals (IPIs) of stimulation waveforms.

FIG. 10 shows embodiments of a graphical user interface (GUI) for selecting stimulation parameters. The illustrated GUI presents a representation of an implanted electrode lead 1002 and may provide an anatomical reference 1004 indicating the anatomical location of the lead. For example, the anatomical reference 1004 in the illustrated embodiment shows that the electrodes of the implanted lead span the region between the T8/T9 intervertebral space to the T10 vertebrae. The GUI also displays an electrode assignment bar 1006, which indicates the function assigned to each of the electrodes on the displayed lead. In the illustrated GUI, the lead is configured for bipolar stimulation with the top electrode operating as a cathode for 100% of the delivered current and the third electrode operating as an anode for 100% of the delivered current. The sixth electrode is designated R1 (for recording), indicating that the electrode is configured for recording electrical signals, such as electrospinogram (ESG) signals, as explained in more detail below. The GUI includes an indicator 1008 indicating the center point of stimulation (CPS). The GUI includes a stimulation adjustment 1010, allowing the stimulation geometry (i.e., bipole, tripole size and location) to be adjusted. It should be noted that while a single electrode lead is displayed in the illustrated GUI, the GUI may be configured to display multiple implanted electrodes, paddle leads, case electrodes, and other electrode configurations. Likewise, while bipolar stimulation is illustrated, other pole configurations may be used, such as tripolar and monopolar. Moreover, the IPG case or another internal or external electrode may be used as a return.

The illustrated GUI also includes a sub-display 1012, which can display an indication of the temporal firing patterns of the neural fibers in response to the stimulation. In the illustrated embodiment, the sub-display 1012 displays an ESG trace recorded at the recording electrode. The sub-display 1012 may display additional or other data. For example, the sub-display may display temporal firing patterns of neural sub-populations (based on modelling or measured data), such as illustrated in FIGS. 9A-9C.

A second window of the GUI includes a parameter selection 1014 where stimulation parameters can be entered/displayed. In the illustrated GUI the parameter selection is set for a manual mode such that stimulation parameters may be manual entered/selected. Other embodiments may operate according to more automated modes whereby one or more of the stimulation parameter are automatically loaded. For example, one automated mode may be a frequency-duration mode (illustrated as "Freq-Duration") which may auto-populate a pulse width that is predicted to be effective for a given selected frequency, for example. Such automated modes may be informed based on the frequency-pulse width relationships described in the above incorporated '904 Application, for example.

During programming and/or during initial operating room implantation of the electrodes, the patient may be tested with several candidate waveforms at a desired frequency, pulse width, IPI, stimulation geometry, and amplitude. The candidate waveforms may be evaluated based on one or more metrics to determine the waveform(s) having the highest efficacy. The waveforms may be selected based on patient feedback, perception threshold and/or ESGs recorded using the recording electrode (R1 in the illustration). For example, each waveform with a distinct IPI can be rated based on patient sensation and comfort and the ratings may be displayed to the programmer in a rating display 1016 of the GUI in the form of a "star rating," where the number of stars indicate highest satisfaction. Thus, waveforms may be selected based on metrics such as sensation, pain relief, power consumption, and the like. Other metrics may relate to how well the recorded ESG trace corresponds to a desired ESG trace. The GUI may include one or more metric selections 1018 allowing the programmer to select which metric to use to optimize the waveform shape, including the IPI. The IPI may be selected based on a composite, sum, or average of a plurality of selection metrics. Machine learning (e.g., clustering and/or regression algorithms) can be used to derive waveform shapes based on multiple dimensions of selection metrics. The GUI may also include a manual IPI input 1020, whereby a user can manually enter an IPI value. Thus, embodiments of the disclosure provide methods and systems for determining optimal stimulation parameters, including determining a best IPI to use for stimulation. Generally, the IPI may be any time value. Example IPIs are typically in the microsecond to millisecond range. For example, the IPI may be configurable from 10 microseconds to 500 microseconds. As another example, the IPI may be 0.5 ms to 2.5 ms.

Figure 11:
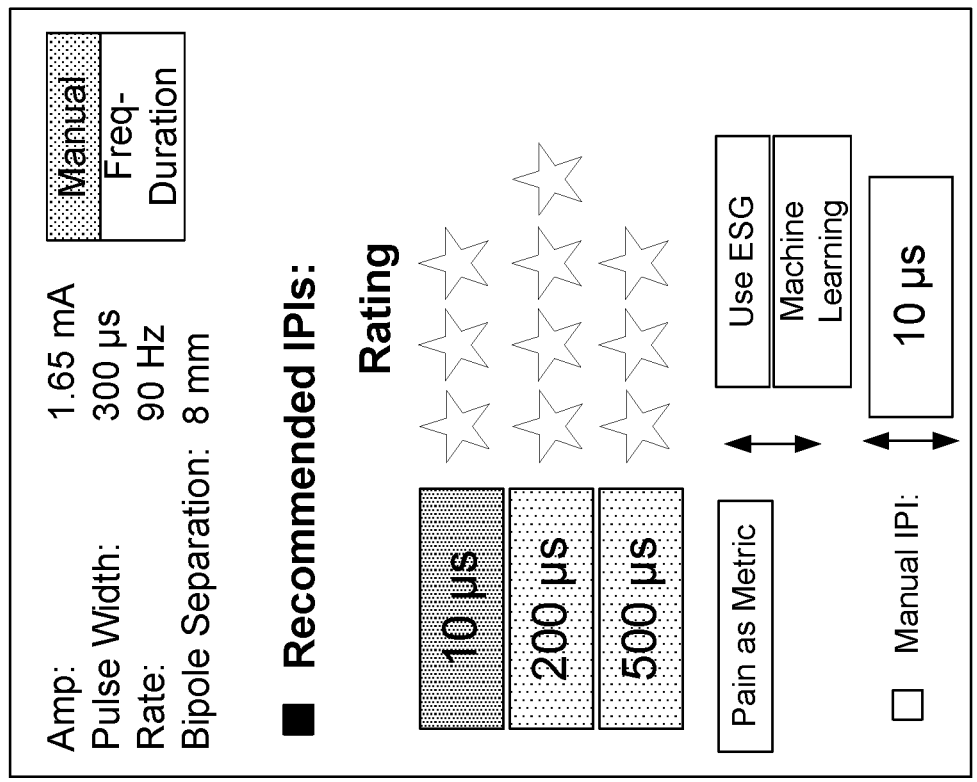
FIG. 11 shows an embodiment of a GUI for optimizing interphase intervals (IPIs) of stimulation waveforms based on expected neural effects.

Correlations can be determined between waveform parameters, such as IPI, and physiological effects. For example, some IPIs may result in suppression of side effects (like unpleasant paresthesia) whereas other IPIs result in beneficial asynchronous temporal firing patterns that correlate to pain relief. For example, referring to FIG. 9A, the applied waveform can be said to "suppress" the activity of fibers at depth E. Thus, "suppression" may denote suppression of neural responses, as well as suppression of a physiological effect. Correlations between the IPIs may be determined based on patient feedback and ratings. Alternatively (or in addition), such correlations may be determined based on modeling of the patient's neural tissues. Temporal patterns predicted by modeling and/or known to occur during specific waveform settings may be pre-loaded into the external clinician's programmer. If the efficacy of temporal patterns is known (e.g., by implementing a dorsal horn model or from experimental data), then patterns may be selected based on predicted physiological effects. According to some embodiments, the GUI may reflect such correlations by denoting (for example, by color coding) the effect that an IPI would be expected to generate. Referring to FIG. 11, assume that through patient ratings or through modeling it is determined that IPIs of 10 μs and 50 μs provide suppression of side effects and that IPIs of 200 μs and 500 μs provide asynchronous temporal firing patterns associated with pain relief. The GUI is color coded to reflect such observed or expected results. For example, the user may select such color coding as the patient provides feedback and rating information. Alternatively, the correlations between the IPIs and the expected results may be stored within the system, in look-up tables, for example.

Figure 12A:
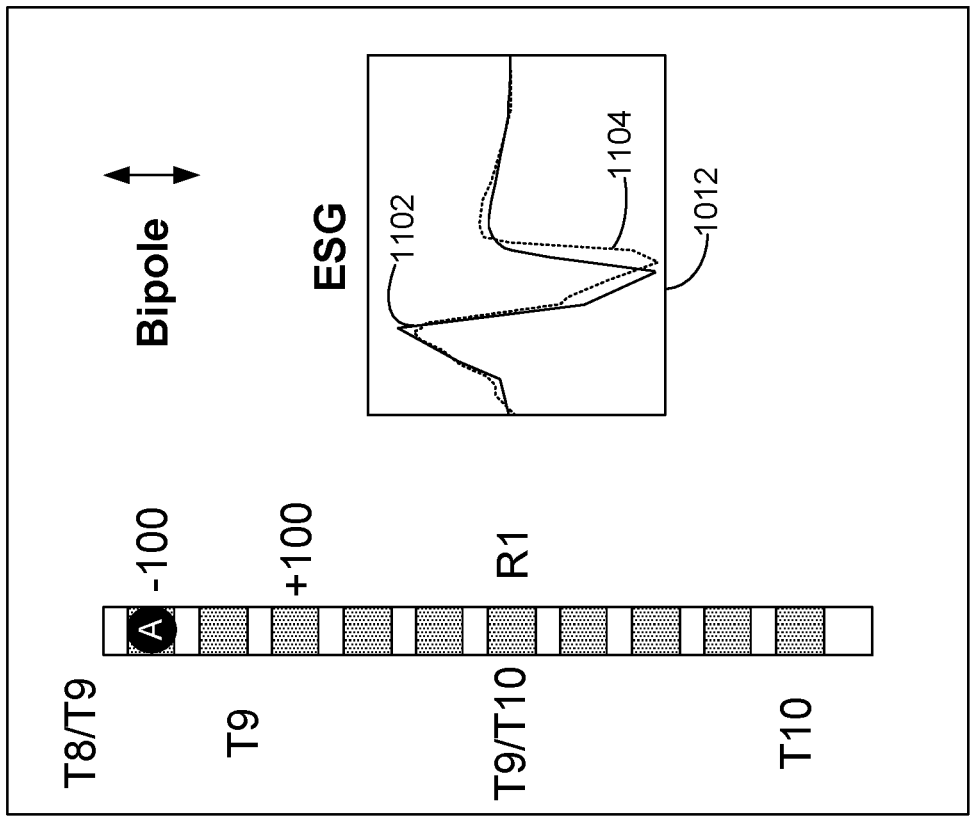
FIGS. 12A and 12B show an embodiment of a GUI for optimizing interphase intervals (IPIs) of stimulation waveforms based on electrospinogram (ESG) measurements.
Figure 12A:
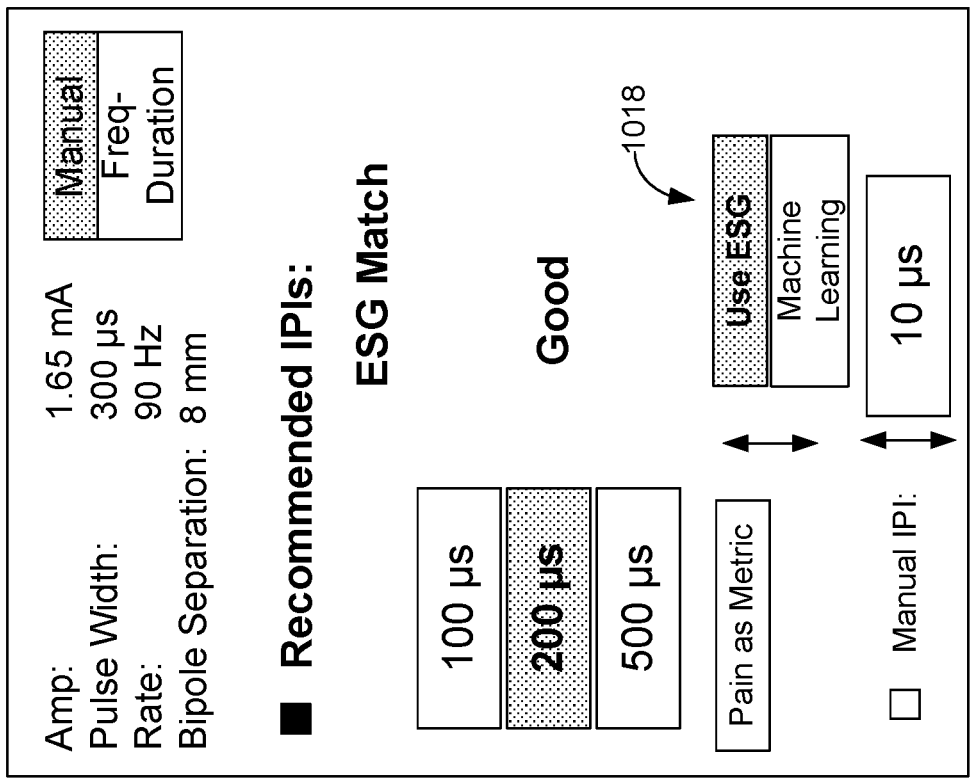
Figure 12B:
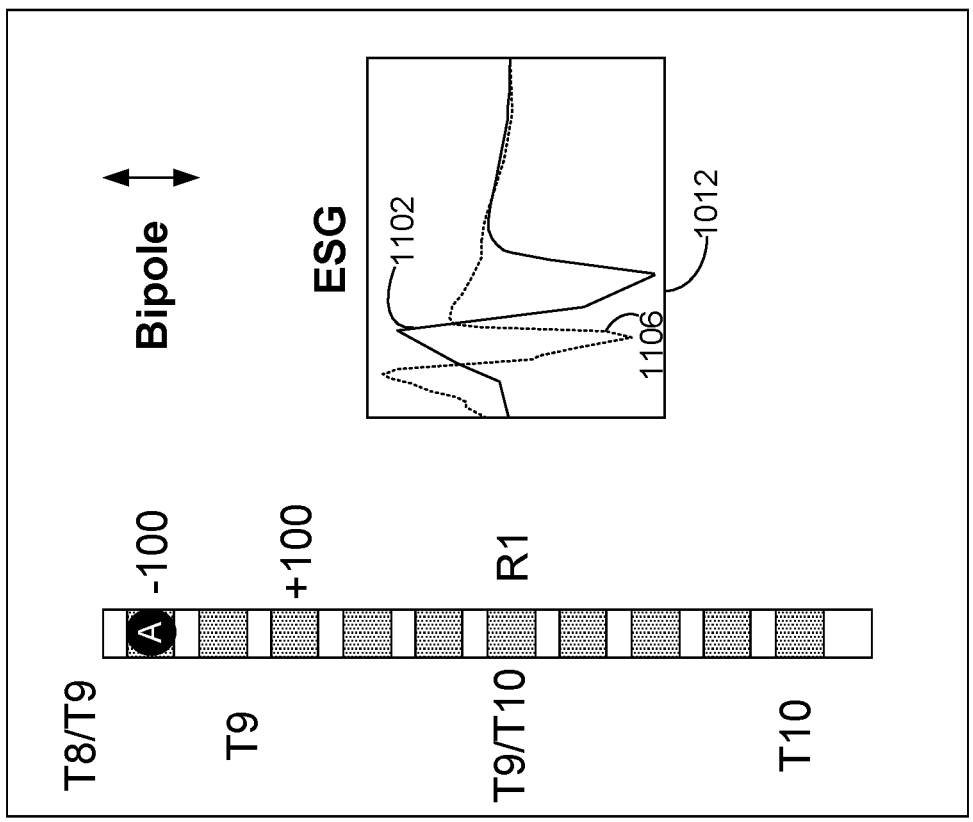
Figure 12B:
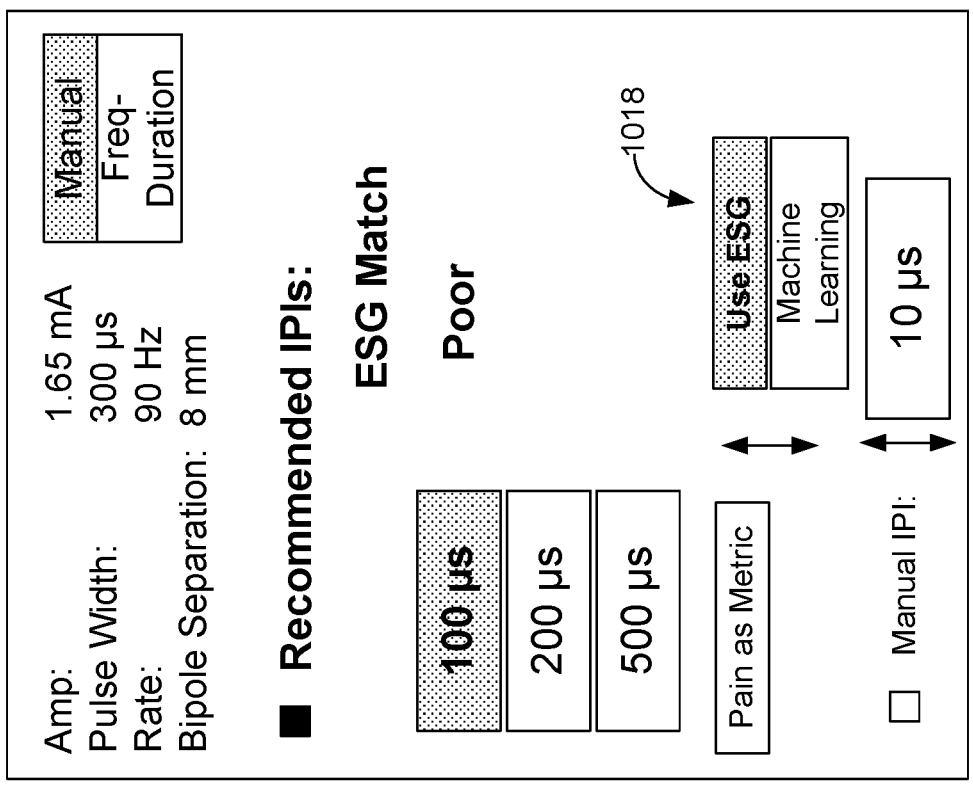

FIG. 12A illustrates an embodiment wherein the ESG trace is used as a metric to determine an IPI that is expected to provide effective therapy. Notice that the "Use ESG" button is selected in the bank of metric selections 1018. The sub-display 1012 shows an ESG trace 1102 in solid line. Assume ESG trace 1102 corresponds to a stimulation parameter set that is determined or predicted to have a beneficial outcome for the patient. For example, during calibration at high stimulation amplitudes (i.e., supra-perception amplitudes), ESG trace 1102 may correspond to signals recorded at the R1 electrode when stimulation parameters are used that result in adequate paresthesia coverage of the patient's pain areas. Now the clinician is attempting to find sub-perception stimulation parameters (i.e., lower amplitude stimulation) that results in a similar ESG trace. As reflected in the GUI, stimulation using an IPI of 200 μs results in a (normalized) ESG trace 1104 (dotted line) that substantially overlaps with the target ESG 1102. Contrast the GUI windows illustrated in FIG. 11A with those shown in FIG. 11B, wherein an IPI of 100 μs is used. As shown in FIG. 11B, an IPI of 100 μs results in an ESG trace 1106 that poorly overlaps with the target ESG trace 1102. As mentioned here, the target ESG traces may be determined using a calibration/fitting procedure or they may be based on patient feedback/rating. Alternatively, target ESG traces may be preloaded based on modeling predictions and/or a template generated (e.g., averaged) from previously recorded data.

Figure 13A:
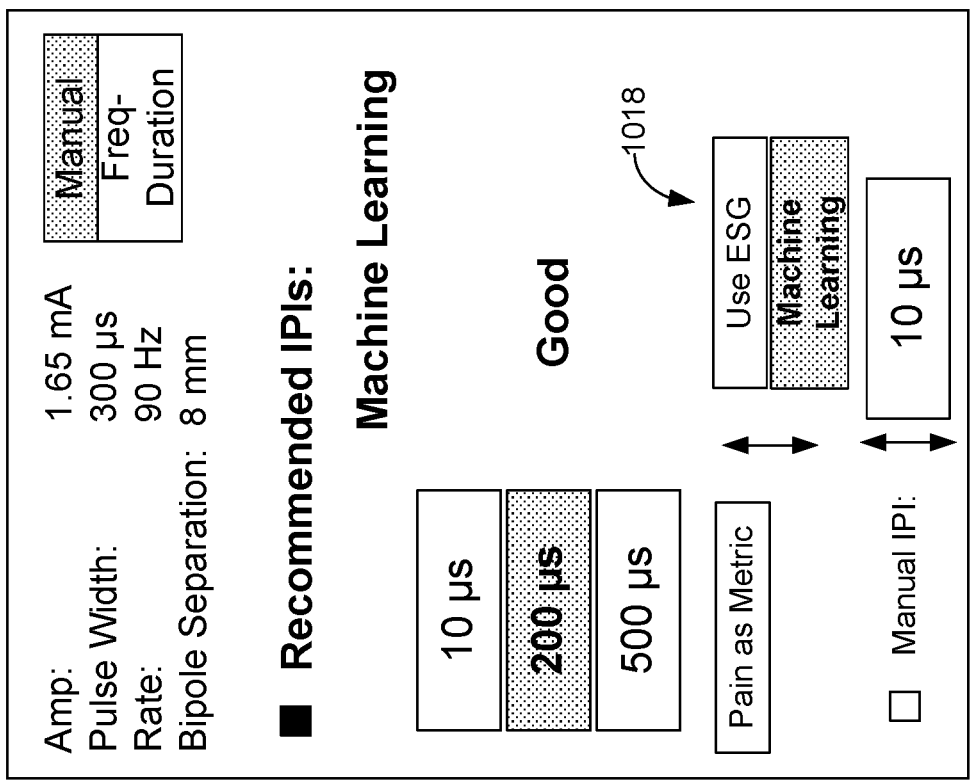
FIGS. 13A and 13B show an embodiment of a GUI for optimizing interphase intervals (IPIs) of stimulation waveforms based on temporal firing patterns of neural elements.
Figure 13A:
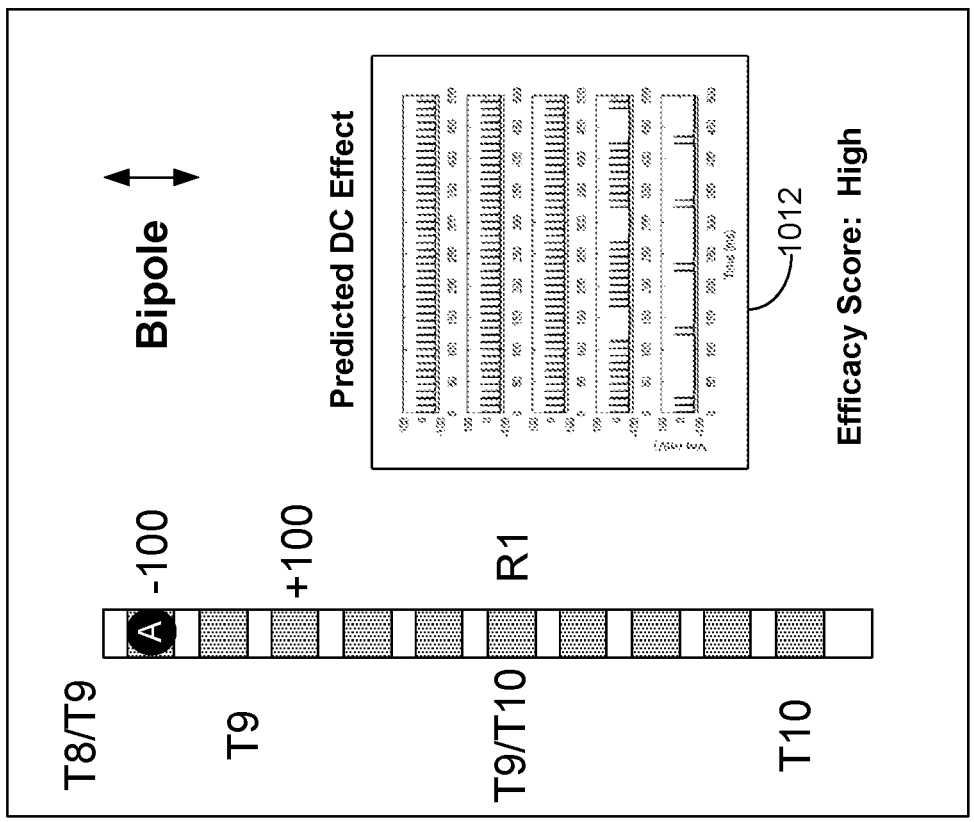
Figure 13B:
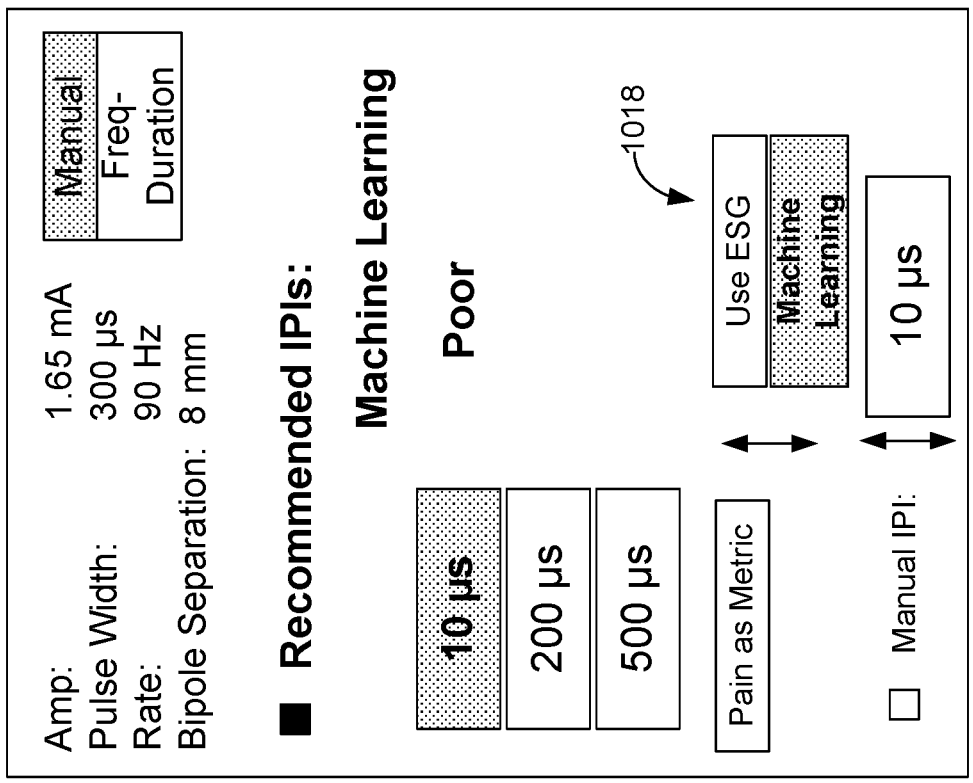

FIGS. 13A and 13B illustrate embodiments wherein predicted or machine learning-generated temporal firing patterns corresponding to specific waveform settings are used to select stimulation waveforms. In FIG. 13A notice that "Machine Learning" is selected in the bank of metric selections 1018. When 200 μs is selected as the IPI, the sub-display 1012 displays a predicted temporal firing pattern corresponding to the IPI. An efficacy score associated with the temporal firing pattern may be displayed. The efficacy associated with the temporal firing pattern may be based on modeling, for example, or may be based on experimental data. In the embodiment illustrated in FIG. 13A, the temporal firing pattern is known to be associated with high efficacy, and thus, an efficacy shore or "High" is displayed. By contrast, in FIG. 13B, the temporal firing pattern corresponding to an IPI of 10 μs is known to be associated with low efficacy. Thus, an efficacy score of "Low" is displayed.

Figure 14:
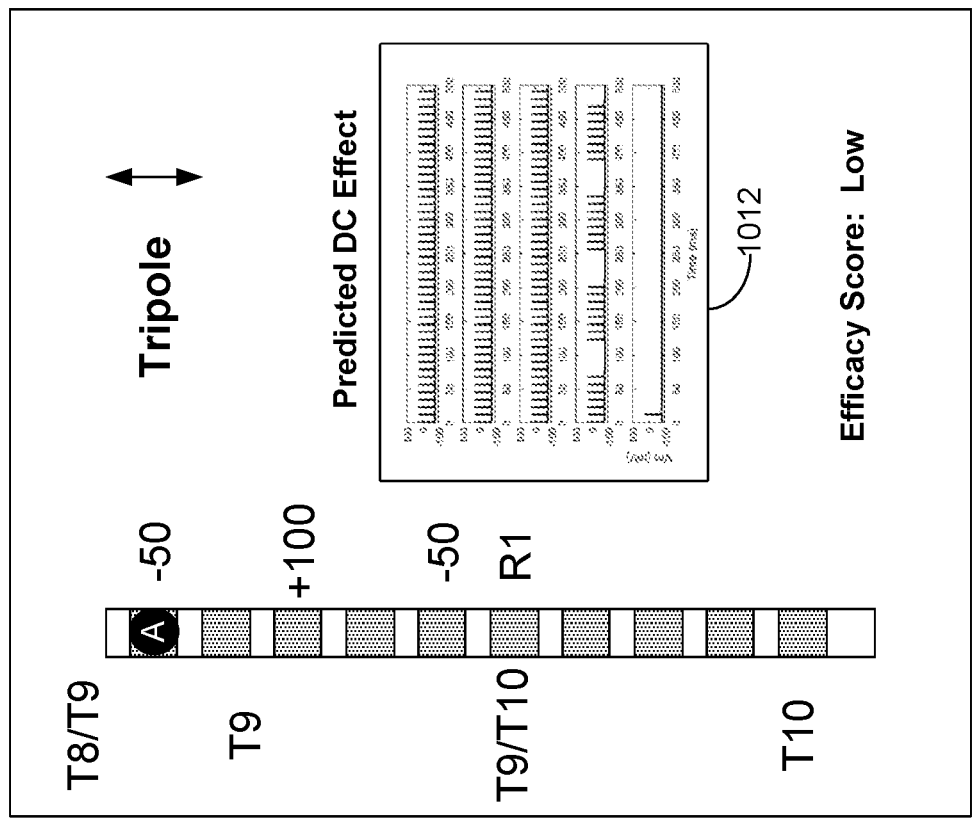
FIG. 14 shows an embodiment of a GUI for optimizing interphase intervals (IPIs) of stimulation waveforms based utilizing tripolar stimulation.
Figure 14:
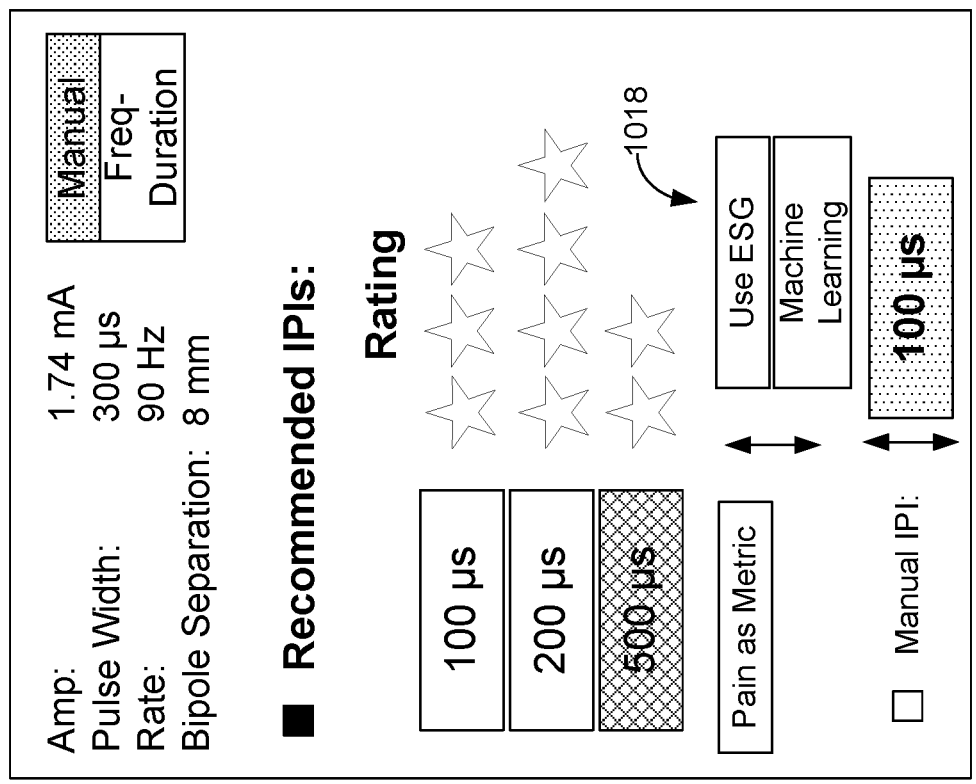

As mentioned above, stimulation geometries other than bipoles are available. The stimulation geometry may be used to vary the temporal firing patterns evoked by the stimulation. The stimulation geometry may be chosen based on what works best for the paresthesia search and specific amplitudes, pulse widths, IPIs, and anticipated temporal firing patterns may be paired with each stimulation geometry. FIG. 14 illustrates an embodiment wherein the GUI is used to configure a stimulation geometry that is a tripole. In the illustrated embodiment, the third electrode operates as an anode for 100% of the current and the first and fifth electrodes each operate as cathodes for 50% of the current. According to some embodiments, it may be known that certain IPI's do not work well for certain stimulation parameters, such as with certain stimulation geometries. Thus, embodiments of the GUI may remove the choice to select certain IPIs. Notice in FIG. 14 that the button to select an IPI of 500 μs is grayed out, indicating that 500 μs is an IPI known to give rise to problems, such as side effects, when used with the other selected stimulation parameters. The decision to "withhold" or "lock-out" some possible IPIs may be based on modeling of the temporal firing patterns that would be evoked using the IPIs in conjunction with the other stimulation parameters. The decision may alternatively (or additionally) based on patient feedback and/or on pre-loaded data from other patients, the cloud, etc. Relationships between IPIs and other stimulation parameters (such as IPI/parameter combinations that are not suitable) may be stored in look-up tables, for example. Moreover, some combinations of stimulation parameters might preclude certain IPIs simply because they are not possible. For example, for a given pulse width and frequency, it might simply be impossible to use certain IPIs because there is not enough time during the period of the waveform to use some IPIs. The system may include internal logic that withholds such physically impossible waveforms. Moreover, some waveform configurations, such as those involving a short pulse width or a monophasic pulse, may not be compatible with IPI variation. Thus, the IPI configuration may be locked out for those parameter sets. However, according to some embodiments, the user may still select a manual IPI feature to configure IPIs.

Figure 15A:
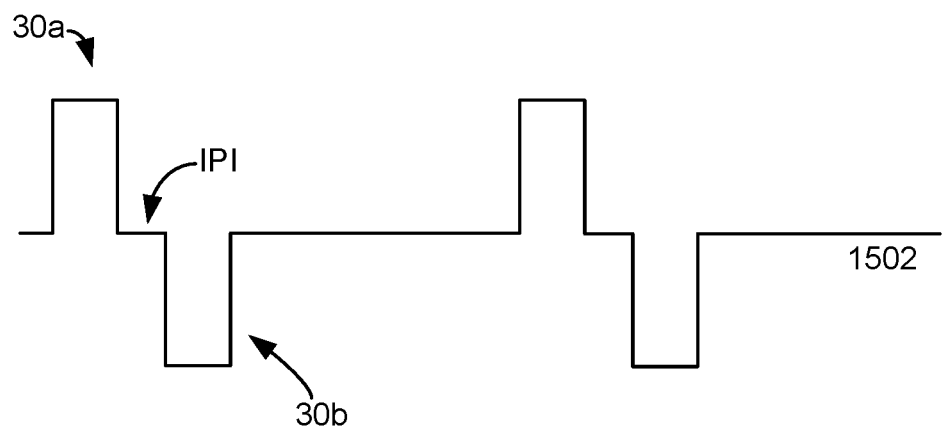
FIGS. 15A and 15B show examples of waveforms.
Figure 15B:
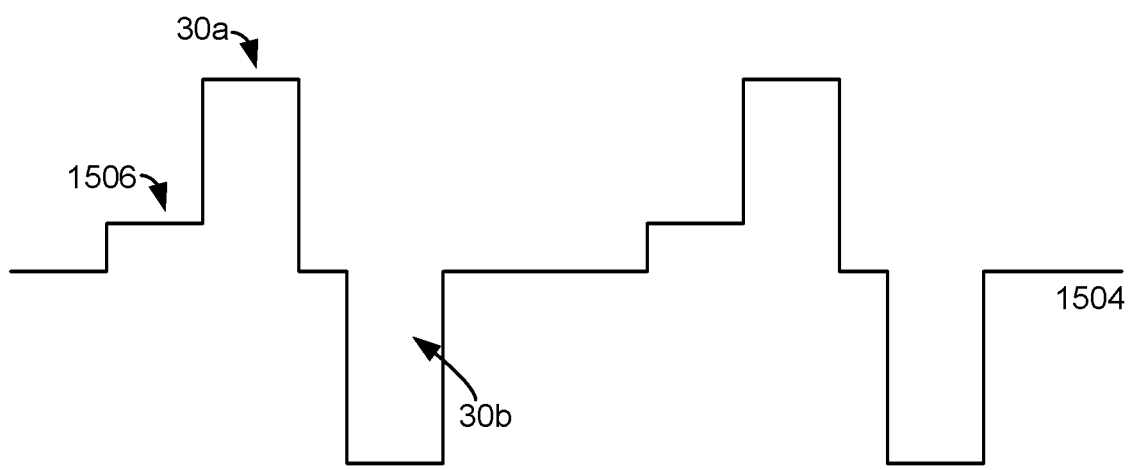

It should be noted here that aspects of the disclosure concern stimulation programs (which prescribe waveforms) that define a plurality of sequential pulses, wherein each pulse comprises a first phase having a first polarity and a second phase having a second polarity opposite of the first polarity. An example of a waveform 1502 having a first phase having a first polarity and a second phase having a second polarity opposite of the first polarity is illustrated in FIG. 15A. In FIG. 15A, the first phase 30*a* and the second phase 30*b* are separated by an IPI. However, it should be noted that more complicated waveforms are possible and within the scope of this disclosure. For example, waveforms may have multiple sequential phases of the same polarity preceding an interphase interval (IPI) and/or multiple sequential phases following the IPI. FIG. 15B illustrates a waveform 1504 having a pre-pulse 1506 of low amplitude preceding the "first phase" 30*a*. In the waveform 1504, phase 30*a* is still considered the first phase having a first polarity and phase 30*b* is considered a second phase having a second polarity, as those terms are used herein. In other words, as used herein, the term "first phase having a first polarity" refers to a phase having the highest absolute amplitude preceding an IPI and the term "second phase having a second polarity" refers to a phase having the highest absolute amplitude following an IPI wherein the polarity is opposite that of the first phase.

Various aspects of the disclosed techniques, including processes implementable in the IPG or ETS, or in external devices such as the clinician programmer or external controller to render and operate the GUI, can be formulated and stored as instructions in a computer-readable media associated with such devices, such as in a magnetic, optical, or solid-state memory. The computer-readable media with such stored instructions may also comprise a device readable by the clinician programmer or external controller, such as in a memory stick or a removable disk, and may reside elsewhere. For example, the computer-readable media may be associated with a server or any other computer device, thus allowing instructions to be downloaded to the clinician programmer system or external controller or to the IPG or ETS, via the Internet for example.

Note that some of the applications to which this present disclosure claims priority, which are incorporated by reference above, are directed to concepts (e.g., selecting optimal stimulation parameters, and in particular stimulation parameters that cause sub-perception at lower frequencies) that are relevant to what is disclosed. Techniques in the present disclosure can also be used in the context of these priority applications. For example, aspects of the stimulation parameters can be chosen in accordance to the methods described in the incorporated references.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for programming an implantable medical device (IMD) having a plurality of electrodes implantable in a patient's spinal column, the method comprising:
  selecting a stimulation program defining a plurality of sequential pulses, wherein each pulse comprises a first phase having a first polarity and a second phase having a second polarity opposite of the first polarity, wherein the first and second phases are separated by an interphase interval (IPI);
  applying the stimulation program to the patient's spinal cord using a plurality of differing IPIs;
  based on a determination of effectiveness of the stimulation program using the plurality of differing IPIs, determining a best IPI for addressing the patient's pain; and
  using the best IPI in programming the IMD,
  wherein the determination of effectiveness of the stimulation program using the plurality of differing IPIs is based on an electrospinogram (ESG) trace.

2. The method of claim 1, wherein the determination of effectiveness of the stimulation program using the plurality of differing IPIs is based on patient feedback.

3. The method of claim 2, wherein the patient feedback comprises rankings of the stimulation program using the plurality of differing IPIs.

4. The method of claim 1, wherein the ESG trace is measured using one or more electrodes of the plurality of electrodes.

5. The method of claim 1, wherein the determination of effectiveness of the stimulation program using the plurality of differing IPIs based on an ESG trace comprises comparing ESG traces obtained using the stimulation program with each of the differing IPIs to a target ESG trace.

6. The method of claim 5, wherein the target ESG trace corresponds to stimulation settings that provide effective paresthesia coverage of the patient's pain.

7. The method of claim 5, wherein the target ESG trace corresponds to settings that provide effective pain relief without paresthesia.

8. The method of claim 5, further comprising obtaining a target ESG using supra-perception stimulation and wherein the determination of the effectiveness of the stimulation program using the one or more differing IPIs comprises using sub-perception stimulation.

9. The method of claim 5, wherein the target ESG trace corresponds to stimulation that provides an effective temporal firing pattern of neural elements.

10. The method of claim 1, further comprising determining the plurality of differing IPIs.

11. The method of claim 1, wherein applying the stimulation program using the plurality of differing IPIs comprises using a graphical user interface (GUI) to select the plurality of differing IPIs.

12. The method of claim 11, wherein the GUI is configured to provide a ranking of the effectiveness of the stimulation program using each of the plurality of differing IPIs.

13. The method of claim 11, wherein the GUI is configured to provide an indication of an expected physiological and/or clinical effect associated with the stimulation program using the plurality of differing IPIs.

14. The method of claim 1, wherein the second phase is actively driven.

15. The method of claim 1, wherein the second phase is passively driven.

16. The method of claim 1, wherein the plurality differing IPIs are from 10 microseconds to 500 microseconds.

17. The method of claim 1, further comprising determining a best stimulation geometry to produce a desired physiological effect.

* * * * *